United States Patent
Kruger

(10) Patent No.: US 6,216,025 B1
(45) Date of Patent: Apr. 10, 2001

(54) THERMOACOUSTIC COMPUTED TOMOGRAPHY SCANNER

(75) Inventor: Robert A. Kruger, Indianapolis, IN (US)

(73) Assignee: Optosonics, Inc., Indianapolis, IN (US)

( * ) Notice: Subject to any disclaimer, the term of this patent is extended or adjusted under 35 U.S.C. 154(b) by 0 days.

(21) Appl. No.: 09/243,004

(22) Filed: Feb. 2, 1999

(51) Int. Cl.⁷ .............................. A61B 5/05; A61B 6/00; G01N 24/00
(52) U.S. Cl. ..................... 600/407; 73/625; 128/915; 600/443
(58) Field of Search ...................... 600/407, 437, 600/443, 444, 445, 448; 128/915, 916; 73/602, 603, 620, 624, 625, 626, 627, 628, 629

(56) References Cited

U.S. PATENT DOCUMENTS

| | | | |
|---|---|---|---|
| 3,603,303 | * | 9/1971 | Stouffer ............................... 600/437 |
| 4,059,010 | | 11/1977 | Sachs ...................................... 73/596 |
| 4,206,763 | * | 6/1980 | Pedersen .............................. 600/445 |
| 4,233,988 | | 11/1980 | Dick et al. ....................... 128/915 X |
| 4,246,784 | | 1/1981 | Bowen ................................. 178/736 |
| 4,255,971 | | 3/1981 | Rosencwaig ........................... 73/606 |
| 4,267,732 | | 5/1981 | Quate .................................... 73/606 |
| 4,385,634 | | 5/1983 | Bowen ............................. 128/653.1 |
| 4,481,821 | | 11/1984 | Chamuel ............................... 73/617 |
| 4,484,820 | | 11/1984 | Rosencwaig ........................... 374/6 |
| 4,485,819 | * | 12/1984 | Igl ....................................... 600/445 |
| 4,509,368 | * | 4/1985 | Whiting et al. ...................... 73/624 |
| 4,545,385 | * | 10/1985 | Pirschel ............................... 600/445 |
| 4,681,120 | | 7/1987 | Kunii ............................... 178/915 X |
| 4,874,251 | | 10/1989 | Thomas et al. ....................... 374/45 |
| 4,950,897 | | 8/1990 | Mandelis et al. .................... 250/334 |
| 5,070,733 | | 12/1991 | Nagata et al. ........................ 73/602 |
| 5,170,666 | | 12/1992 | Larsen .................................. 73/571 |
| 5,348,002 | | 9/1994 | Caro ................................ 128/664 X |
| 5,402,786 | | 4/1995 | Drummond ................ 128/660.01 X |
| 5,615,675 | | 4/1997 | O'Donnell et al. ............... 128/653.1 |
| 5,657,754 | | 8/1997 | Rosencwaig ........................ 128/633 |
| 5,713,356 | | 2/1998 | Kruger ............................. 128/653.1 |

FOREIGN PATENT DOCUMENTS

| | | | |
|---|---|---|---|
| 26 43 126 | 3/1977 | (DE) | .............................. G01N/29/00 |
| 3925312 | 4/1990 | (DE) | . |
| 4446390 | 7/1996 | (DE) | . |
| 0 018 771 | 4/1980 | (EP) | . |
| 318 283 | 5/1989 | (EP) | .............................. G01N/29/04 |
| 0 582 384 | 7/1992 | (EP) | . |
| PCT 83/00009 | 1/1983 | (WO) | . |
| WO97/27801 | 8/1997 | (WO) | .............................. A61B/8/13 |

OTHER PUBLICATIONS

Kruger, Photo acoustic ultrasound , Med. Phys. 21(1): 127–131, 1994.

(List continued on next page.)

Primary Examiner—Sang Paik
(74) Attorney, Agent, or Firm—Wood, Herron & Evans, L.L.P.

(57) ABSTRACT

Methods and apparatus for measuring and characterizing the localized electromagnetic wave absorption properties of biologic tissues in vivo, using incident electromagnetic waves to produce resultant acoustic waves. Multiple acoustic transducers arranged on an rotatable imaging bowl are acoustically coupled to the surface of the tissue for measuring acoustic waves produced in the tissue when the tissue is exposed to a pulse of electromagnetic radiation. The multiple transducer signals are then combined to produce an image of the absorptivity of the tissue, which image may be used for medical diagnostic purposes. Specific mathematical reconstruction procedures are described for producing images from transducer signals. Specific arrangements of transducers are illustrated, and noise reduction techniques are described.

101 Claims, 10 Drawing Sheets

OTHER PUBLICATIONS

Kruger et al., Photo–coustic ultrasound: pulse production and detection of 0.5% liposyn, Med. Phys. 21 (7): 1179–1184, 1994.

Kruger et al., Photoacoustic Ultrasound: Theory and Experimental Results, SPIE vol. 2134A: 114–121, 1994.

Nasoni et al., Thermoacoustic Emission by Deeply Penetrating Microwave Radiation, Poc. of IEEE Ultrasonic Symposium, 633–38, 1984.

Bowen et al., Some Experimental Results of the Thermoacoustic Imaging of Tissue Equivalent Phantom Materials, Proc. of IEEE Ultrasonic Symposium 2: 823–27, 1981.

Bowen, Radiation–Induced Thermoacoustic Soft Tissue Imaging, Proc. of IEEE Ultrasonic Symposium 2: 817–822, Jun., 1981.

Hunter et al., Acoustic signals of nonthermal origin from high energy protons in water, *J. Acoust. Soc. Am.* 69(9), 1557–1562, Jun. 1981.

Bowen, Acoustic Radiation Temperature of Non–Invasive Thermometry, *Automedica*, vol. 8, 247–267, 1987.

Hebden et al., Tomographic Imaging Using Picosecond Pulses of Light, SPIE vol. 1443, *Medical Imaging V: Image Physics* 294–300, 1991.

Beard et al. Characterization of post mortem arterial tissue using time–resolved photoacoustic spectrosopy at 436, 461 and 532 nm. *Phys. Med Biol. 42* (1997) 177–198.

Shan et al., Modeling of a photoacoustic probe designed for medical applications, Ultrasonics 34 (1996) 575–577.

Ossoff et al., Computer–Assisted Surgical Techniques: A Vision for a Future of Otolaryngology—Head and Neck Surgery, *Jrnl of Otolaryngology*, vol. 23, No. 5 (1994) 354–359.

Chen et al., A new laser–ultrasound transducer for medical applications, Ultrasonics vol. 32, No. 4 (1994) 309–313.

Appledorn et al., Energy Deposition Patterns in the Breast a 1064 nm for Photoacoustic Ultrasound, SPIE vol. 2708 (1996) 655–664.

Fang et al., Microwave Applicators for Photoacoustic Ultrasonography, SPIE vol. 2708 (1996) 645–654.

Kruger et al., Photoacoustic ultrasound (PAUS)—Reconstruction tomography., *Med. Phys. 22* (10), Oct. 1995, pp. 1605–1609.

Liu et al., Simulation of Photoacoustic Signal Production in Human Breast Phantoms at 1064 nm, SPIE vol. 2708, 1996, pp. 312–322.

* cited by examiner

THERMOACOUSTIC COMPUTED TOMOGRAPHY SCANNER

CROSS REFERENCE TO RELATED APPLICATIONS

This application is related to copending application Ser. No. 09/076,385 filed May 12, 1998, entitled THERMOACOUSTIC TISSUE SCANNER, and to copending application Ser. No. 09/076,968 filed May 13, 1998, entitled PHOTOACOUSTIC BREAST SCANNER, which is a divisional of Patent Cooperation Treaty application designating the U.S. Ser. No. 97/17832, filed Oct. 1, 1997, which is a continuation of application Ser. No. 08/719,736, filed Oct. 4, 1996, now U.S. Pat. No. 5,713,356, issued Feb. 3, 1998, all of the foregoing being filed in the name of the same inventor as the present application and assigned to the same assignee as the present application, and all of the foregoing hereby incorporated by reference into this application.

STATEMENT AS TO FEDERALLY SPONSORED RESEARCH

The U.S. Government has certain rights in this invention pursuant to grant no. CA68825 made by the National Institute of Health.

FIELD OF THE INVENTION

The present invention relates to imaging properties of tissue based upon differential absorption of electromagnetic waves in differing tissue types by photo-acoustic techniques.

BACKGROUND OF THE INVENTION

It is well established that different biologic tissues display significantly different interactions with electromagnetic radiation from the visible and infrared into the microwave region of the electromagnetic spectrum. While researchers have successfully quantified these interactions in vitro, they have met with only limited success when attempting to localize sites of optical interactions in vivo. Consequently, in vivo imaging of disease at these energies has not developed into a clinically significant diagnostic tool.

In the visible and near-infrared regions of the electromagnetic spectrum, ubiquitous scattering of light presents the greatest obstacle to imaging. In these regions, scattering coefficients of 10–100 mm$^{-1}$ are encountered. Consequently, useful numbers of unscattered photons do not pass through more than a few millimeters of tissue, and image reconstruction must rely on multiply-scattered photons. While efforts persist to use visible and infrared radiation for imaging through thick tissue (thicker than a few centimeters), clinically viable imaging instrumentation has not been forthcoming.

In the microwave region (100–3000 MHZ), the situation is different. Scattering is not as important, since the wavelength (in biologic tissue) at these frequencies is much greater than the "typical" dimension of tissue inhomogeneities ($\approx 1$ $\mu$m). However, the offsetting effects of diffraction and absorption have forced the use of long wavelengths, limiting the spatial resolution that can be achieved in biologic systems. At the low end of the microwave frequency range, tissue penetration is good, but the wavelengths are large. At the high end of this range, where wavelengths are shorter, tissue penetration is poor. To achieve sufficient energy transmission, microwave wavelengths of roughly 2–12 cm (in tissue) have been used. However, at such a long wavelength, the spatial resolution that can be achieved is no better than roughly ½ the microwave length, or about 1–6 cm.

In vivo imaging has also been performed using ultrasound techniques. In this technique, an acoustic rather than electromagnetic wave propagates through the tissue, reflecting from tissue boundary regions where there are changes in acoustic impedance. Typically, a piezoelectric ceramic chip is electrically pulsed, causing the chip to mechanically oscillate at a frequency of a few megahertz. The vibrating chip is placed in contact with tissue, generating a narrow beam of acoustic waves in the tissue. Reflections of this wave cause the chip to vibrate, which vibrations are converted to detectable electrical energy, which is recorded.

The duration in time between the original pulse and its reflection is roughly proportional to the distance from the piezoelectric chip to the tissue discontinuity. Furthermore, since the ultrasonic energy is emitted in a narrow beam, the recorded echoes identify features only along a narrow strip in the tissue. Thus, by varying the direction of the ultrasonic pulse propagation, multi-dimensional images can be assembled a line at a time, each line representing the variation of acoustic properties of tissue along the direction of propagation of one ultrasonic pulse.

For most diagnostic applications, ultrasonic techniques can localize tissue discontinuities to within about a millimeter. Thus, ultrasound techniques are capable of higher spatial resolution than microwave imaging.

The photoacoustic effect was first described in 1881 by Alexander Graham Bell and others, who studied the acoustic signals that were produced whenever a gas in an enclosed cell is illuminated with a periodically modulated light source. When the light source is modulated at an audio frequency, the periodic heating and cooling of the gas sample produced an acoustic signal in the audible range that could be detected with a microphone. Since that time, the photoacoustic effect has been studied extensively and used mainly for spectroscopic analysis of gases, liquid and solid samples.

It was first suggested that photoacoustics, also known as thermoacoustics, could be used to interrogate living tissue in 1981, but no subsequent imaging techniques were developed. The state of prior art of imaging of soft tissues using photoacoustic, or thermoacoustic, interactions is best summarized in Bowen U.S. Pat. No. 4,385,634. In this document, Bowen teaches that ultrasonic signals can be induced in soft tissue whenever pulsed radiation is absorbed within the tissue, and that these ultrasonic signals can be detected by a transducer placed outside the body. Bowen derives a relationship (Bowen's equation 21) between the pressure signals $p(z,t)$ induced by the photoacoustic interaction and the first time derivative of a heating functions, $S(z,t)$, that represents the local heating produced by radiation absorption. Bowen teaches that the distance between a site of radiation absorption within soft tissue is related to the time delay between the time when the radiation was absorbed and when the acoustic wave was detected.

Bowen discusses producing "images" indicating the composition of a structure, and detecting pressure signals at multiple locations, but the geometry and distribution of multiple transducers, the means for coupling these transducers to the soft tissue, and their geometrical relationship to the source of radiation, are not described. Additionally, nowhere does Bowen teach how the measured pressure signals from these multiple locations are to be processed in order to form a 2- or 3-dimensional image of the internal structures of the soft tissue. The only examples presented are 1-dimensional in nature, and merely illustrate the simple relationship between delay time and distance from transducer to absorption site.

The above-referenced U.S. Pat. No. 5,713,356, filed by the present inventor, details a diagnostic imaging technique in which pulses of electromagnetic radiation are used to excite a relatively large volume of tissue and stimulate acoustic energy. Typically, a large number of such pulses (e.g., 100 to 100,000), spaced at a repetition interval, are generated to stimulate the tissue. The above-referenced patent application discloses methods for measuring the relative time delays of the acoustic waves generated by a sequence of such pulses, and for converting these time delays into a diagnostic image.

SUMMARY OF THE INVENTION

The present invention improves upon what is disclosed by the above-referenced U.S. Patent in several ways. First, the present invention utilizes appropriate materials and acoustic shielding techniques within the scanner to minimize stray echoes and sources of noise. Furthermore, multiple noise cancellation techniques are utilized to improve image quality; these techniques include collecting a noise pattern and subtracting of this pattern from the collected signal, and modulating the duration of time between imaging pulses of electromagnetic radiation to randomize the effect of acoustic echoes from serial pulses. Also, a new filtering technique is applied to compensate for the frequency response of the transducers and analog circuitry used to collect photoacoustic signals. These improvements collectively result in a substantial enhancement of the images that can be rendered by the thermoacoustic scanner.

The above and other objects and advantages of the present invention shall be made apparent from the accompanying drawings and the description thereof.

BRIEF DESCRIPTION OF THE DRAWING

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF SPECIFIC EMBODIMENTS

Figure 1:
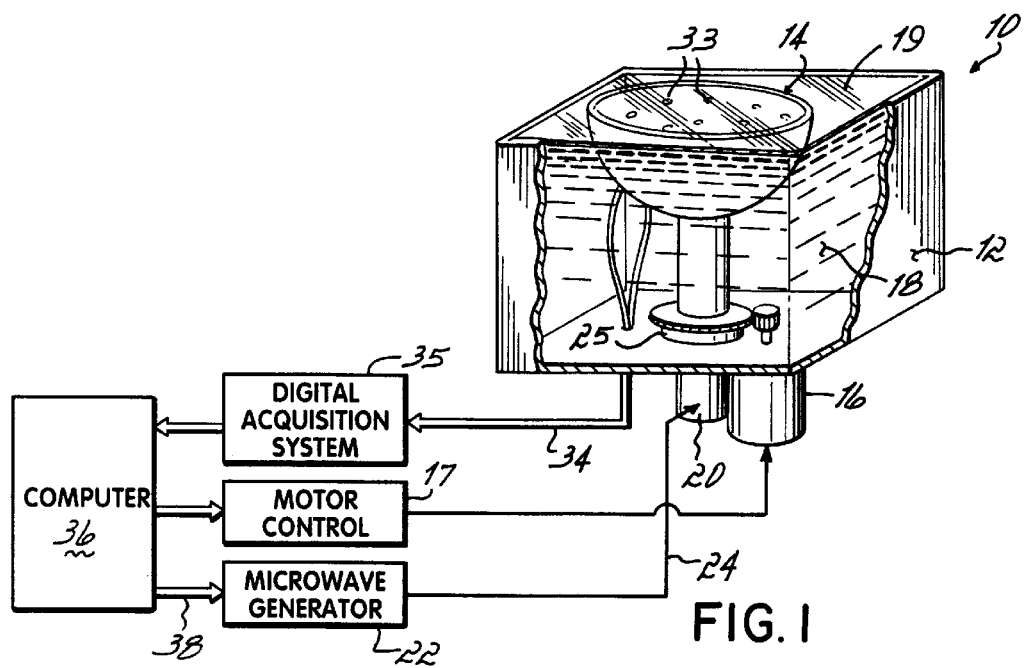
FIG. 1 illustrates a thermoacoustic breast scanner in accordance with principles of the present invention and, in block diagram form, the electronic components used therewith.

FIG. 1 illustrates a photoacoustic breast scanner 10 in accordance with one embodiment of the present invention, which displays several key elements for successful photoacoustic scanning of the female human breast.

A human breast is placed within an imaging tank 12 roughly centered over an imaging bowl 14 located within the tank. Imaging tank 12 contains fluid or semi-solid media 18 having dielectric properties which are close to that of "average" breast tissue at the microwave (or radio wave) frequencies used to stimulate photoacoustic emission within the breast. Media 18 also has acoustic properties close to that of breast tissue. Examples of suitable media would be salinated water, alcohol or mineral oil. The breast may be placed directly within media 18, or alternatively, the media 18 may be contained within tank 14 by a flexible sheet 19, for example of Kapton or polyethylene having a thickness of 0.002 inches, on the surface of the tank coupled to the breast. Sheet 19 ensures good mechanical contact and acoustic coupling between the tissue of the breast and the media 18 in tank 14.

Extending from the imaging bowl 14 is a cylindrical acoustic waveguide 20 which is used as a microwave antenna. A microwave generator 22, i.e., a source of pulse microwave or radio wave energy, is coupled to antenna 20 through standard high voltage connectors and a transmission line 24. One suitable microwave generator is manufactured by Amplifier Systems, North Ridge, Calif., as part no. CE-20K-4333. The generator produces a 25 kilowatt peak power RF pulse having a width of 0.5 microseconds with a rise time of 100 nanoseconds to 90% of peak power.

Antenna 20 is large enough to irradiate all or a large fraction of the breast volume to be imaged. A cylindrically-shaped waveguide 2.4 inches in diameter is suitable. Further details on the waveguide are found below with reference to in FIG. 3.

One purpose of dielectric coupling media 18 is to improve the penetration of the microwave energy into the breast tissue. Because the breast is compressed against the surface of tank 12, there is a continuous interface between coupling media 18 and the tissue of the breast, uninterrupted by air gaps. An air gap, or any other physical discontinuity having a corresponding discontinuity in dielectric properties, will cause a large fraction of the microwave energy to reflect away from the interface (and thus away from the surface of the breast), rather than penetrate into the breast. By matching the dielectric properties of the breast and media 18, and eliminating air gaps, such discontinuities are reduced, improving microwave penetration into breast.

As noted above, microwave generator 22 delivers short-duration pulses of radiation to the breast. Each radiation burst causes localized heating and expansion of the breast tissue exposed to the microwave energy. Tissue heating and expansion will be greatest in those regions of the breast tissue which are most absorptive of the microwave energy. If a region of tissue within the breast (e.g., a tumor) is particularly more absorptive than the surrounding tissue, the region will expand relatively more rapidly and extensively than the surrounding tissue, creating an acoustic wave which will propagate through the tissue. These acoustic waves are manifested as longitudinal pressure waves, containing acoustic frequencies ranging from very low frequencies to approximately the reciprocal of the electromagnetic pulse length. For a one-half microsecond irradiation pulse, this maximum acoustic frequency would be 2 million cycles per second, or two megahertz (MHZ). Acoustic wavefronts produced by electromagnetic irradiation of absorptive regions within the breast travel through the tissue at a velocity of sound propagation $v_s$ which is approximately 1.5 mm/$\mu$s.

Any of several different microwave frequencies may be used, but frequencies in the range of 200–600 MHZ are likely to be particularly effective. At these frequencies, energy penetration is good, absorption is adequate, and differential absorption between different types of tissue, e.g. fat and muscle, is high. It has also been reported that cancerous breast tissue absorbs 2–5 times as much electromagnetic energy than normal breast tissue when stimulated with frequencies in the range of 300 to 500 MHZ. This phenomenon has been attributed to an increase in bound water and sodium within malignant cells.

Another important consideration for thermoacoustic imaging is that the relative signal-to-noise ration (SNR) that can be achieved in imaging water-containing tissues is expected to peak near 434 MHZ. This is based on models of RF power absorption proposed by Foster and Shepps, from which the SNR can be computed as a function of frequency for a malignant mass with a bound water fraction of 0.7, embedded in normal tissue with a bound water fraction of 0.8. According to this model the peak SNR is in the range of 200–600 MHZ.

The frequency of 434 MHZ, specifically, has been approved by the FCC for use in hyperthermia treatments, and accordingly is available and may be used in photoacoustic imaging in accordance with the present invention. Imaging might also be performed at the FCC approved frequency of 915 MHZ. Furthermore, it has been reported that the electrical conductivity of malignant tissue and normal tissue may vary by a factor of fifty. Accordingly, low frequency electromagnetic radiation could also be used to stimulate varied energy absorption and acoustic responses in tissue.

As noted above, imaging tank 12 is filled with coupling media 18, and media 18 is selected to have an acoustic impedance and velocity of sound propagation which are close to that of a "typical" human breast.

Distilled and deionized water is an effective media for this purpose. The breast is compressed against sheet 19, thus ensuring good mechanical coupling from the breast to the media 18 within tank 12, and allowing acoustic energy to freely pass from the breast into tank 12.

An array of sixty-four acoustic transducers 33 is located within imaging bowl 14 in tank 16. The transducers should be evenly spaced across the array. Details on the positioning of the transducers are discussed below in connection with FIG. 6.

Transducers 33 on bowl 14 detect acoustic pressure waves that are induced within the breast by the short irradiation pulse, and travel from emission sites at the velocity of sound in tissue. The transducers are fabricated so as to be most sensitive to sonic frequencies just below the maximum frequency stimulated by the irradiation pulse noted above.

The sixty-four transducers 33 on bowl 14 are coupled through 64 electronic signal lines 34 to a digital acquisition system 35 and then to a computer circuit 36. Computer 36 is further connected through a control line 38 to activate microwave generator 22 to produce a pulse of microwave energy. Following each pulse of radiation, the time-dependent, acoustic pressure signals recorded by each of the transducer elements are electronically amplified, digitized and stored within digital acquisition system 35, for later delivery to computer 36.

Figure 2:
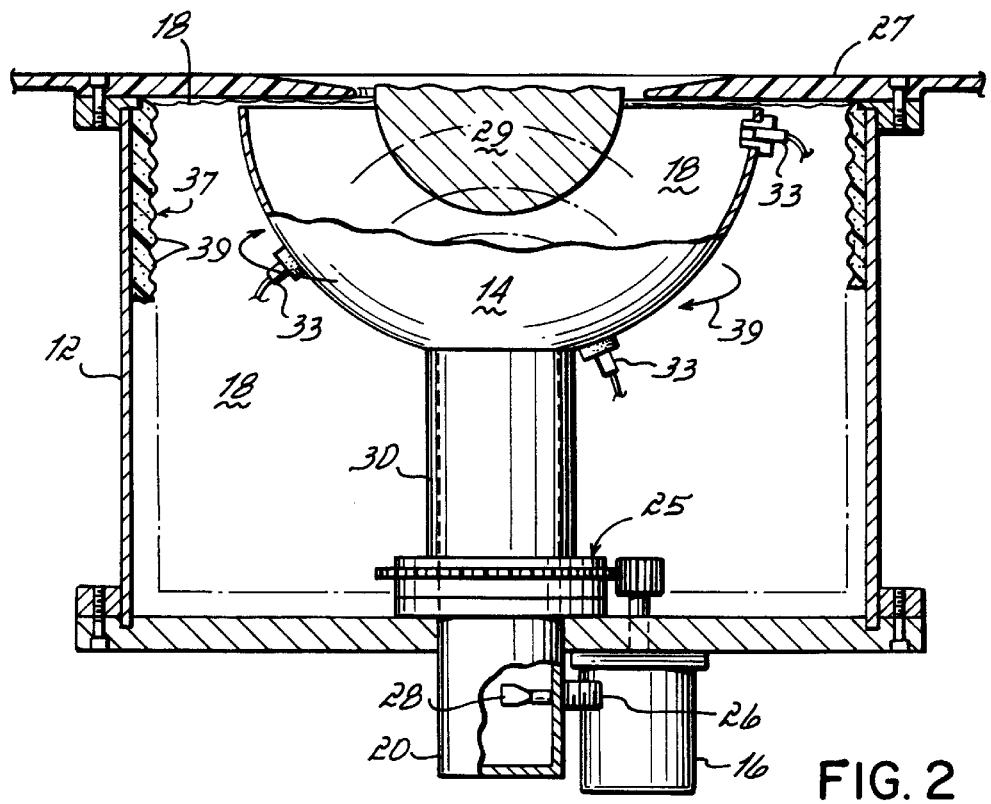
FIG. 2 illustrates the imaging bowl of the thermoacoustic breast scanner of FIG. 1 and a cylindrical microwave waveguide used therewith in accordance with a first embodiment of the present invention.
Figure 3:
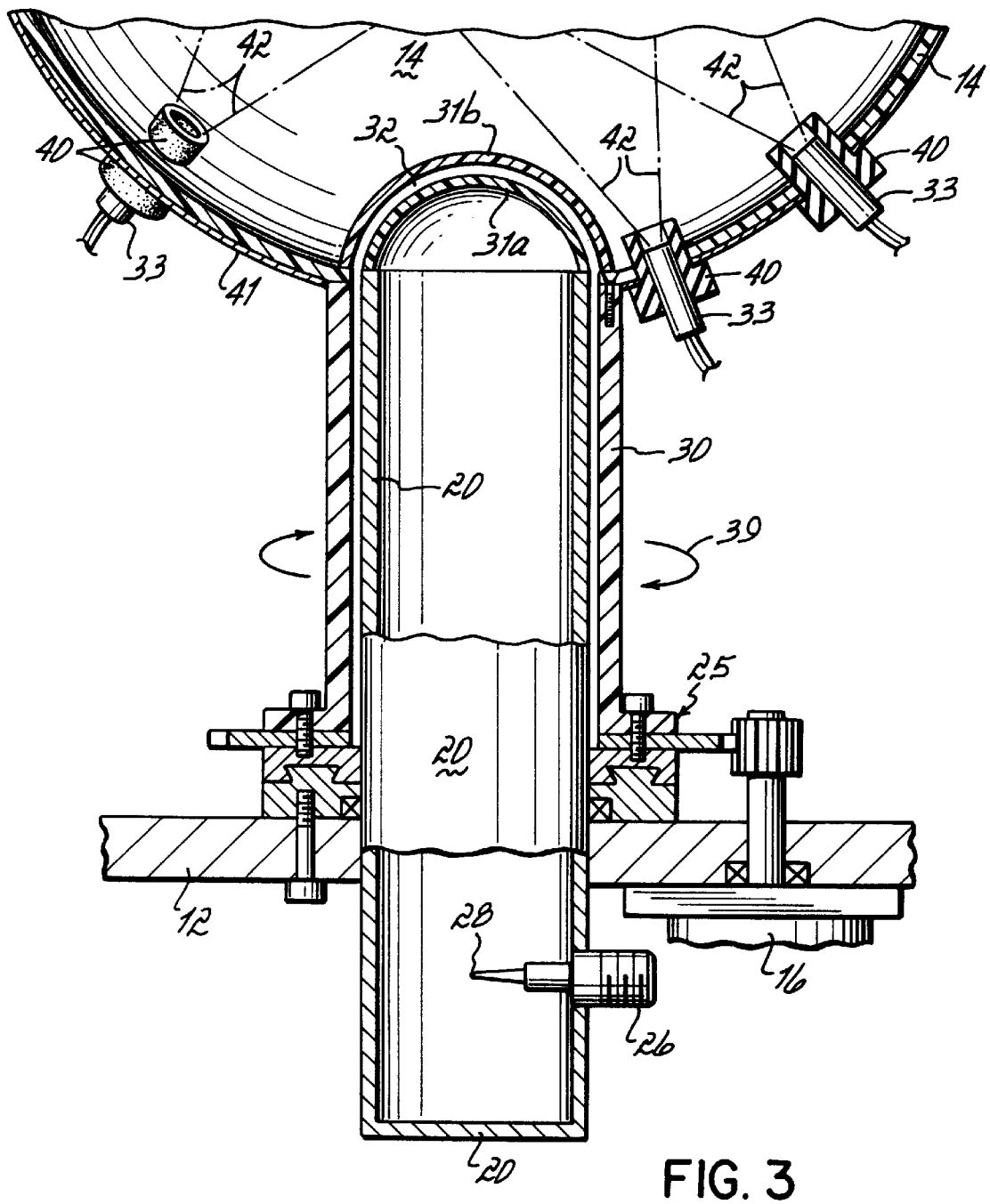
FIG. 3 is a detail view of the imaging bowl of FIG. 2 illustrating the cylindrical waveguide and acoustic shielding of the waveguide and transducers.

As described in further detail below, the imaging bowl and the transducers 33 therein are rotated during the data acquisition, as indicated by arrow 39 (FIGS. 2 and 3). At each angular position of the transducer array, photoacoustic data is collected by the transducers 33 and used to develop a corresponding image. The images may then be combined or superimposed to produce a complete image of the breast. Rotating the imaging bowl in this manner has the effect of increasing the effective number of transducer elements.

The bowl 14 is rotatable through 360 degrees on its axis by a stepping motor 16 under control of motor controller 17. A suitable stepper motor controller (PC board) can be obtained from New England Affiliated Technologies.

Referring now to FIG. 2, further details on the construction of the imaging tank 12, imaging bowl 14 and waveguide 20 can be explained. Imaging tank 12 is secured to a table top 27 which supports the patient. The breast 29 of the patient is positioned as shown in FIG. 2 so that it is coupled by the media 18 in the tank to the acoustic sensors of the imaging bowl 14. Waveguide 20 is journalled in a bearing 25 at the base of imaging tank 12 permitting waveguide 20 and the imaging bowl 14 to which it is attached to rotate freely within tank 12. At the end of waveguide 20 which extends outward from the bottom of tank 12, a coaxial connector 26 is provided for connection to a transmission line 24 leading from the microwave generator 22. The coaxial connector has a conductor which extends internally of waveguide 20 and terminates in an electrode 28.

The imaging bowl has a diameter of 300 millimeters, and is truncated at ±72° relative to the center. In alternative embodiments, such as that shown in FIG. 13, the bowl may be a complete hemisphere and thus truncated at 90° relative to the center. The center of curvature of the bowl is located 30 millimeters above the member surface, and is positioned to be near the center of the breast imaging volume.

Referring now to FIG. 3, it can be seen that waveguide 20 can be formed as a cylindrically shaped conductive waveguide. The waveguide is approximately 2.4 inches in diameter. The length of the waveguide can be chosen arbitrarily. Waveguide 20 has a closed lower end and an open upper end. Electrode 28 is positioned one inch from the closed lower end of waveguide 20. Radiation produced by electrode 28 thus forms radio waves inside of waveguide 20 which radiate from the open upper end of waveguide 20 and into the breast or other tissue positioned adjacent to imaging bowl 14.

As seen in FIG. 3, waveguide 20 may be surrounded by an acoustic baffling medium such as an air pocket to reduce the radiation of acoustic energy produced within the waveguide into the surrounding areas of the imaging tank 12. Acoustic radiation within the imaging tank 12 that does not originate from thermoacoustic effects in the tissue being imaged, will be a source of noise in the imaging process and degrade the resulting image. Accordingly, reductions in acoustic radiation that can be achieved by baffling will improve image quality.

FIG. 3 illustrates that, overlying the open upper end of waveguide 20 are a pair of dome-shaped shells 31a and 31b. Shells 31a and 31b are affixed and sealed at their outer periphery to the end of waveguide 20 and interior surface 30 of imaging bowl 14, respectively, to maintain an air gap 32 between shells 31a and 31b. The air gap 32 between shells 31a and 31b forms an acoustic barrier tending to reflect any acoustic radiation generated within waveguide 20 and block the diffusion of such radiation into imaging bowl 14. Shells 31a and 31b are made of an electromagnetically transparent material such as glass, so that shells 31a and 31b and the air gap therebetween does not reflect any substantial portion of the electromagnetic energy produced by waveguide 20, so that electromagnetic energy from waveguide 20 may pass into the imaging bowl 14 and the tissue being imaged even as acoustic radiation is blocked from passing into imaging bowl 14.

Imaging bowl 14 is supported by an exterior cylindrical shell 30 surrounding waveguide 20. Shell 30 is supported via a bearing assembly 25 by the bottom surface of tank 12. Motor 16 rotates shell 30 and the imaging bowl 14 connected thereto to position the acoustic transducers 33 for imaging.

An alternative antenna may be formed from a wire helix. A suitable helix is of 8 centimeter diameter (the wavelength of 434 MHZ radiation in media 18), at a pitch of approximately 14 degrees. This antenna forms circularly polarized radio waves, and a slowly varying spatial intensity pattern within the imaging volume.

Imaging bowl 14 is preferably formed of a material which substantially damps acoustic energy, and has a density and velocity of sound that is substantially similar to the media 18 within the bowl, so that acoustic energy impinging upon the imaging bowl 14 will be substantially transmitted and not reflected back into imaging bowl 14. Plastic materials such as ABS and polyethylene are well suited to these needs. The purpose of selecting an acoustically transparent material with similar properties to media 18, is to minimize the acoustic radiation that reflects within the imaging bowl 14, and to minimize the amount of acoustic stimulation that arrives at transducers 33 from the imaging bowl itself or from reflections within the imaging bowl 14. The best image quality can be produced when the largest fraction of the stimulation received by transducers 33 is from straight-line radiation from absorptive sites in tissue.

Imaging bowl 14 may also serve as a ground plane for the stimulating electromagnetic radiation to aid in the production of the radiation (particularly where a coil antenna is used), and to focus the energy in the tissue. Polyethylene and ABS plastic have been found to be good materials from an acoustic perspective; however, these materials are nonconductive and thus cannot form an effective ground plane. Accordingly, if a ground plane is desired, the exterior surface of imaging bowl 14 may be coated with a coating 41 of conductive material such as Nickel epoxy. ABS plastic can be more easily vacuum formed than polyethylene and exhibits better adherence to nickel epoxy coatings, accordingly, ABS plastic appears to be a good material to use for the substrate of the imaging bowl 14.

As seen in FIG. 3, transducers 33 are further insulated from acoustic stimulation generated within imaging bowl 14, by surrounding each transducer with a cylindrical collar 40 of an acoustically absorbent material. A suitable baffling medium is butyl rubber that is loaded with metal particles. Another effective baffling medium is paraffin wax. Collar 40 is interposed between imaging bowl 14 and the transducer 33 so that acoustic energy within imaging bowl 14 (due to acoustic emission from waveguide 20 or absorption of acoustic energy by imaging bowl) is insulated from transducer 33. Collar 40 extends into imaging bowl 14 beyond transducer 33; however, collar 40 does not extend into the aperture of transducer 33, i.e., the conical region 42 within which transducer 33 is most sensitive to acoustic signals.

Figure 4:
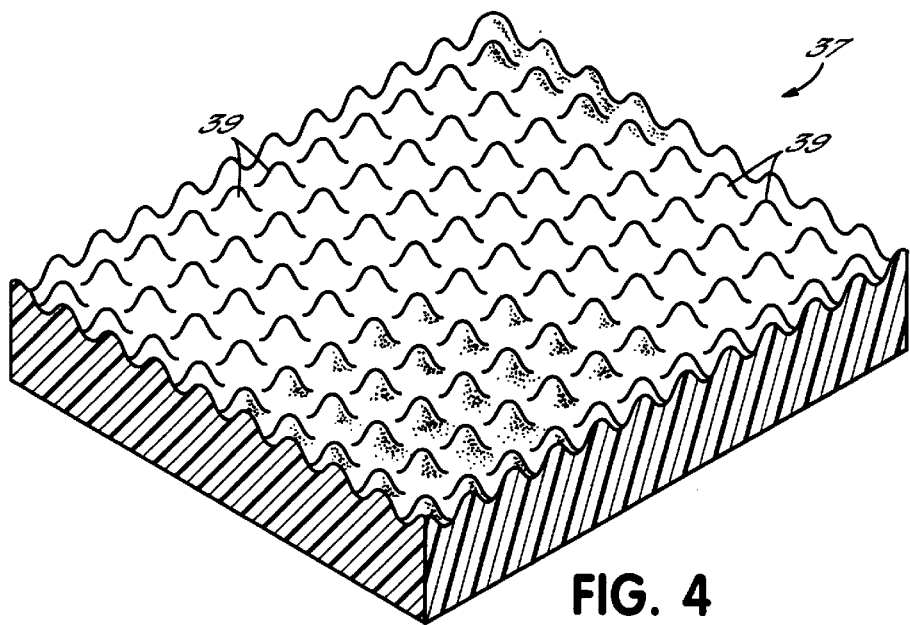
FIG. 4 illustrates an acoustic baffling material used to line the imaging tank of FIGS. 1 and 2.

To further reduce acoustic radiation within imaging tank 12, the interior surfaces of the tank 12 are lined with acoustic baffling material 37 such as butyl rubber. The baffling material 37 is preferably formed with cones 39 on the surface exposed to the interior of tank 12, as shown in FIGS. 2 and 4, so that acoustic energy impinging upon the cones is absorbed into the baffling material and only a minimal amount of energy is reflected.

Figure 5A:
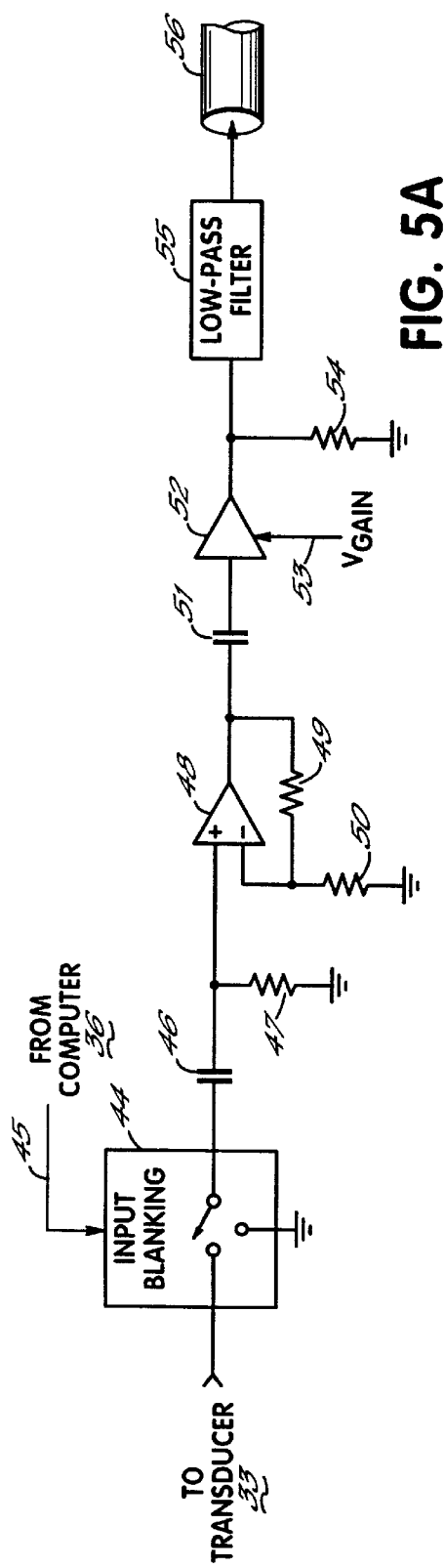
FIG. 5A is a block circuit diagram of the analog amplification stage at each acoustic transducer and FIG. 5B is a block diagram of the circuitry of the digital acquisition system of FIG. 1.

Referring now to FIG. 5A, details of the analog data acquisition circuitry coupled to the transducers can be provided. This circuitry is positioned near to the transducer 33 to maximize signal strength and improve noise immunity. The transducer 33 is coupled to the analog input circuitry through a blanking switch 44. Blanking switch 44, under control of a control signal 45 from the computer system 36, can be controlled to blank the input of the circuitry of FIG. 5A to prevent overdrive and saturation of the analog circuitry. Specifically, the electromagnetic pulse delivered to the tissue within imaging bowl 14 causes the transducers 33 to produce a large magnitude pulse that will overdrive the analog input circuitry. Accordingly, for a brief interval corresponding to the time of each stimulating electromagnetic pulse, computer system 36 causes blanking circuit 44 to blank the input of the analog circuitry of FIG. 5A.

The output of blanking circuit 44 is AC coupled (via a 0.1 microfarad capacitor 46 and 1 kiloohm resistor 47) to the noninverting input of a low noise operational amplifier 48. A suitable op-amp is sold by Maxim as part number 4107. Op-amp 48 is connected to form a noninverting amplifier with a gain of 11, using a 2670 ohm resistor 49 and 26.7 kiloohm resistor 50 connected to the inverting input of op-amp 48. The output of op-amp 48 is AC coupled (via capacitor 51) to the input of a variable gain amplifier 52. A suitable variable gain amplifier 52 is sold by Analog Devices as part number AD603. Amplifier 52 is responsive to a gain control voltage on line 53, which is adjusted to produce an overall gain of 2000 (66 dB) from the combination of amplifier 48 and 52. The output of variable gain amplifier, which is loaded by a 50 ohm impedance 54, is connected to a low pass filter circuit 55. Circuit 55 is a Butterworth filter having a −3 dB bandwidth of 1.6 MHZ. The output of low pass filter circuit 55 connects to a transmission line 56 leading to the appropriate channel of the digital acquisition system 36.

Figure 5B:
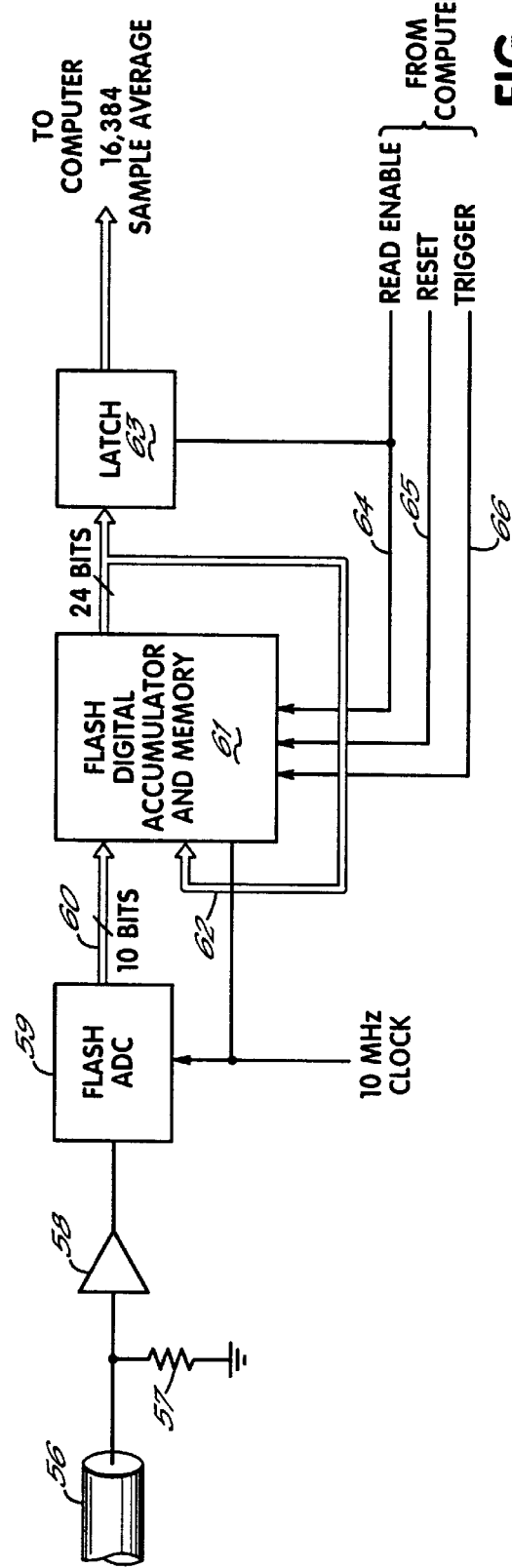

Referring now to FIG. 5B, details of a channel of the digital acquisition system 36 can be explained. The transmission line 56 from the analog input circuitry is connected to a line buffer amplifier 58 and 50 ohm termination resistor 57. The output of line buffer 58 is connected to a 10 bit flash analog to digital converter 59. ADC 59 is clocked at a 10 MHZ clock rate and thus produces 10-bit samples spaced at 0.1 microsecond intervals. A suitable 10-bit flash ADC is sold by Burr-Brown as part number 820. The 10 bit output of ADC 59 is connected to a first input 60 of a digital accumulator and memory circuit 61. Digital accumulator 61, when triggered, receives 2,048 10-bit samples from ADC 59 over a 204.8 microsecond period of time. Accumulator is structured to accumulate data from 1 to 16,384 sequential pulses and form a sample-by-sample sum of 1 to 16,384 2048-sample streams from ADC 59. In the specific embodiment described below, data from 16,384 sequential pulses is gathered, for maximum noise immunity, although a smaller number of pulses could also be used. The output of accumulator 61 is 24-bits wide to permit the accumulation of 16,384 10-bit samples without risk of overflow. The output of accumulator 61 feeds back to a second input 62 so that accumulator 61 can form the sum of a new 10-bit sample stream with sums of previous samples.

Once accumulator 61 has summed 16,384 2048-sample streams from ADC 59, the resulting output from accumulator 61 is passed through a latch/line driver 63 for delivery to computer system 36. For this purpose, computer system 36 produces a read enable signal on line 64 to read the 24-bit sample sums from accumulator 61. Computer system 36 also produces a trigger signal on line 66 to trigger accumulator 61 to receive and accumulate 2048 10-bit samples after an electromagnetic pulse. Computer system 36 also produces a reset signal on line 65 to accumulator 61; after the accumulated results of 16,384 pulses have been received by computer system 36 via latch 63, computer system 36 delivers a reset signal on line 65 to reset accumulator 61 to permit new a sums to be accumulated.

Figure 6:
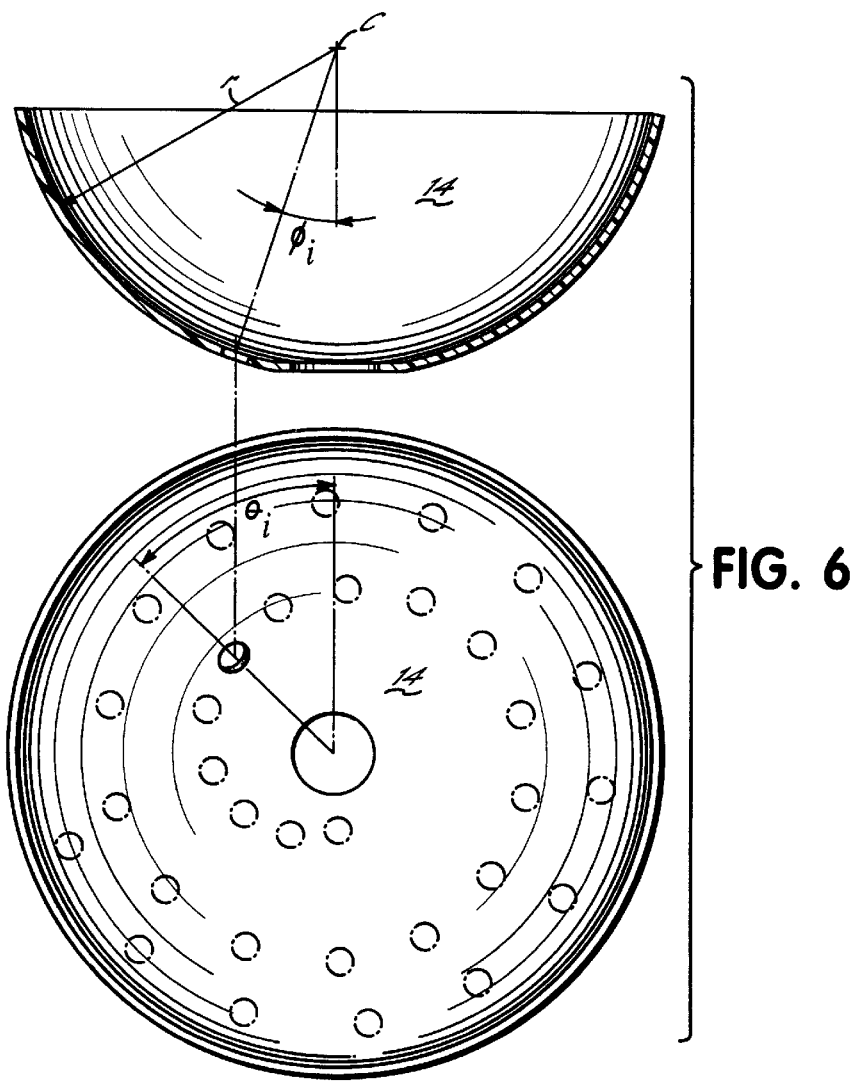
FIG. 6 is an illustration of the coordinate system used in describing the positioning of the transducers in the imaging bowl of FIGS. 1 and 2.

FIG. 6 illustrates the positions of the transducers in the spiral array (some are shown in phantom). The position of each transducer 33 is given by three spherical coordinates ($r,\theta,\phi$) as is illustrated in FIG. 6. Each of the N transducers 33 is on the spherical surface (at a constant radius R), located at a unique ($\theta,\phi$) coordinate, and is oriented on the surface with its axis passing through the center C of the radius of curvature of the spherically curved surface of imaging bowl 14. The $\phi$ positions of the transducers 33 range from a minimum angle of $\phi_{min}$, approximately 16.6 degrees, to a maximum angle of $\phi_{max}$, approximately 72 degrees. It is desirable to maximize this range of angles, i.e., so that $\phi_{max}-\phi_{min}$ is as large as possible, since doing so will enhance the extent to which features in the imaged tissue can be reconstructed in multiple dimensions. (In some embodiments, $\phi_{max}-\phi_{min}$ typically must be less than 45°; however, in the embodiment of FIG. 6, $\phi_{max}-\phi_{min}$ approaches 90°.)

The spiral array will be rotationally stepped to each of sixty-four positions during data acquisition, uniformly spanning 0<$\theta$<360°. The ($\theta,\phi$) positions of each of the N transducers are chosen so that after scanning, the locus of N×M transducer locations produced by the M rotational steps are distributed approximately uniformly over the spherical surface.

Figure 7:
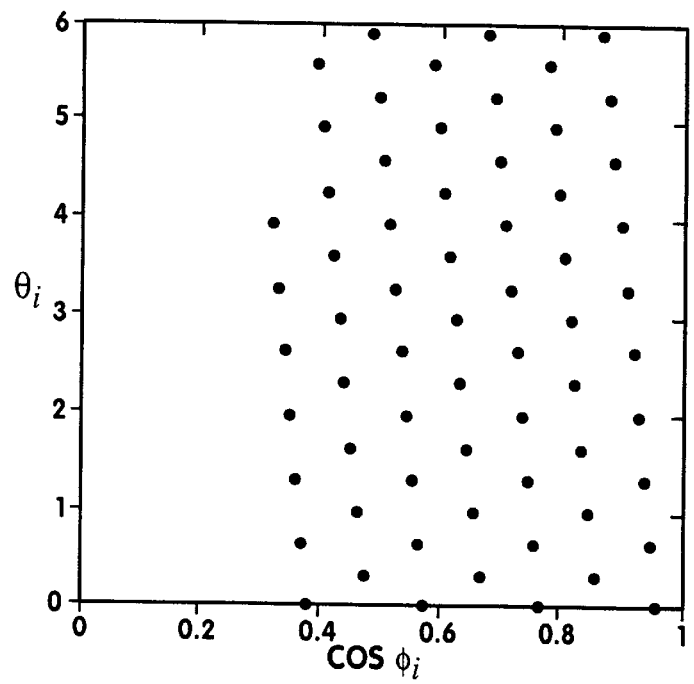
FIG. 7 is a plot of the transducer locations showing their even distribution in $\theta$ and $\cos \phi$.

To accomplish uniform distribution of transducer locations over the spherical surface of the array, an elemental area $\Delta A_i$ on the surface of the hemispherical bowl was associated with each transducer i. In spherical coordinates, $\Delta A_i \approx R^2 \sin \phi_i \Delta\phi_i \Delta\theta_i$, where R=150 millimeters and $\phi_i$ and $\theta_i$ are as shown in FIG. 6. Conceptually, $\Delta A_i$ is associated with the area on the hemisphere bounded by transducer i and its three nearest neighbors. $\Delta\theta_i$ was chosen to be constant for each transducer. Since $\Delta A_i$ and $\Delta\theta_i$ are constant, this implies that $\sin \phi_i \Delta\phi_i = -d(\cos \phi_i) = k$, where k is a constant. k can be computed by observing that the first transducer will be at $\phi_1=16.6$ degrees and the 64$^{th}$ transducer will be at $\phi_{64}=72$ degrees, so $63k=\cos \phi_1-\cos \phi_{64}=0.652$. Therefore, k=0.0103. Choosing $\Delta\theta_i<<2\pi$ resulted in a spiral pattern of transducer placement along the face of the imaging bowl 14. Let N be the number of spirals and N/64 be the number of transducer locations per spiral. For uniform spacing of the transducers over the entire range of $\theta$ and $\cos \phi$ we N/($\cos \phi_1-\cos \phi_{64}$)=64/N or N=6.46. To ensure that all transducers were as physically separated as possible, we chose 64/N= 9.5, or $\Delta\theta=37.9$ degrees. the locations of the transducers chosen in this way are plotted in FIG. 7 as a function of $\theta$ and $\cos \phi$.

After sonic pressure waves are recorded using the transducers and electronics described above, photoacoustic images must be "reconstructed" from multiple pressure signals. The aim is to reconstruct some property of the breast from an ensemble of pressure measurements made externally to the breast. In this case, these measurements are time-dependent pressure signals recorded subsequent to object-irradiation by a short pulse of radiation.

Figure 8:
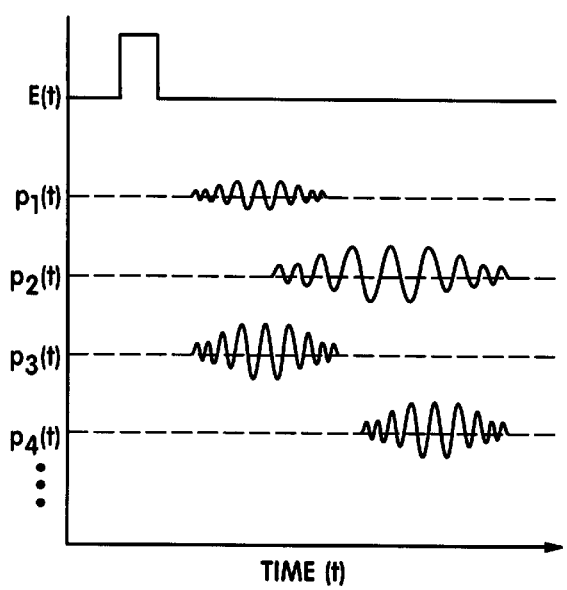
FIG. 8 is an illustration of the acoustic responses produced by tissue and received by transducers after stimulation by an electromagnetic pulse.

As an example, FIG. 8 illustrates the pressure signals $p_i(t)$ that might be produced by four hypothetical transducers in response to pressure waves produced by a short duration of electromagnetic irradiation of tissue. FIG. 8 shows the signal E(t) produced by microwave generator 22 (FIG. 1) is a brief pulse of microwave energy. The resulting acoustic signals produced within the breast or other tissue are subsequently received by each of the transducers, producing signals $p_i(t)$ having differing relative magnitudes and timing, as illustrated.

Figure 9:
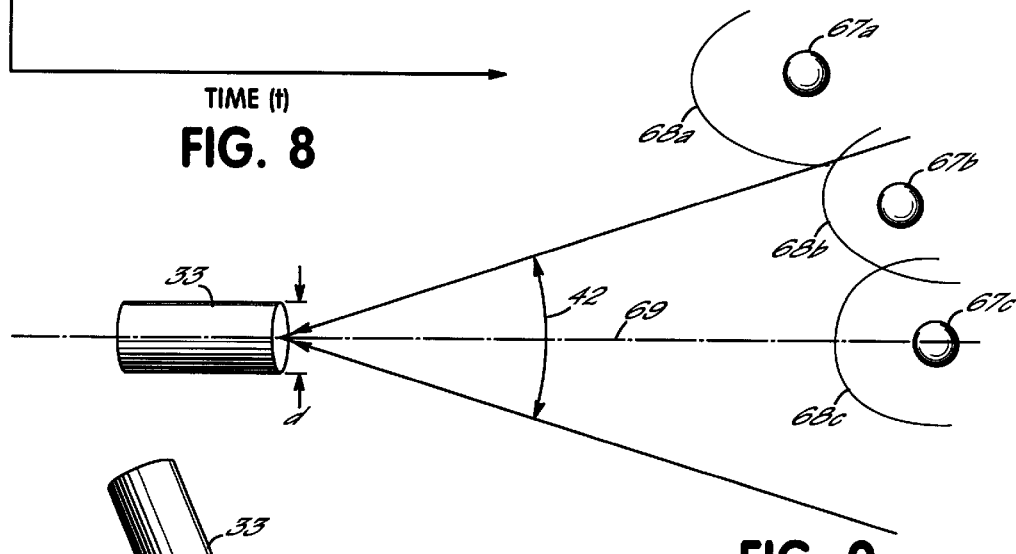
FIG. 9 is an illustration of the receiving aperture of a transducer.

It is important that the transducers be small enough so that they are sensitive to sonic waves that impinge upon the transducers from a wide angle. Referring to FIG. 9, three hypothetical absorbing regions 67a, 67b and 67c are shown in greater detail, along with the respectively corresponding wavefronts 68a, 68b and 68c emitted by these regions, toward a transducer 33. Upon irradiation, each region 67 is the origin of an acoustic pressure wave that travels in all directions. Part of each wave reaches transducer 33 after a delay time.

Transducer 33 is a piezoelectric ceramic chip (or a suitable alternative) having a cross-sectional diameter d exposed to regions 67a, 67b and 67c. Electrical contacts (not shown) attached to the exterior of transducer 33 detect an electrical waveform produced by the chip in response to mechanical vibration, as a result of the piezoelectric property of the ceramic chip.

Because the acoustic energy is transmitted in a wave, transducer 33 is not equally sensitive to the pressure waves from the three absorptive regions. The transducer is most sensitive to acoustic waves from aperture region 42 which lies on axis 69 of transducer 33 (axis 69 being defined by the direction that lies at a 90° angle to the front surface of transducer 33). Transducer 33 is less sensitive to acoustic waves from region outside of aperture 42 because this region is off of axis 69. Past a certain maximum angle, $\theta$, away from axis 69, transducer 33 is substantially insensitive to pressure waves such as those from region 67a.

Maximum angle $\theta$ is given approximately by the relationship $\sin(\theta) \approx v_s\tau/d$, where $v_s$ is the velocity of sound in the relevant medium (here, tissue), $\tau$ is the irradiation pulse length and d is the diameter of the transducer. If a relatively large volume is to be imaged, then $\theta$ should be as large as possible (small d), but if d is too small, the transducer will produce a signal too weak to be electrically detectable without excessive noise. In general, the transducer diameter should be in the range of $v_s\tau<d<4v_s\tau$. The velocity of sound in tissue is approximately 1.5 mm/µs. Thus, for a nominal pulse width, $\tau$, of 1 µs, d should ideally be in the range of approximately 1.5 to 6.0 millimeters. Specialized transducers have been fabricated by Panametrics of Waltham, Mass., having a flat face 13 millimeters in diameter and center frequency of approximately 1.0 MHZ and used with success.

Figure 10:
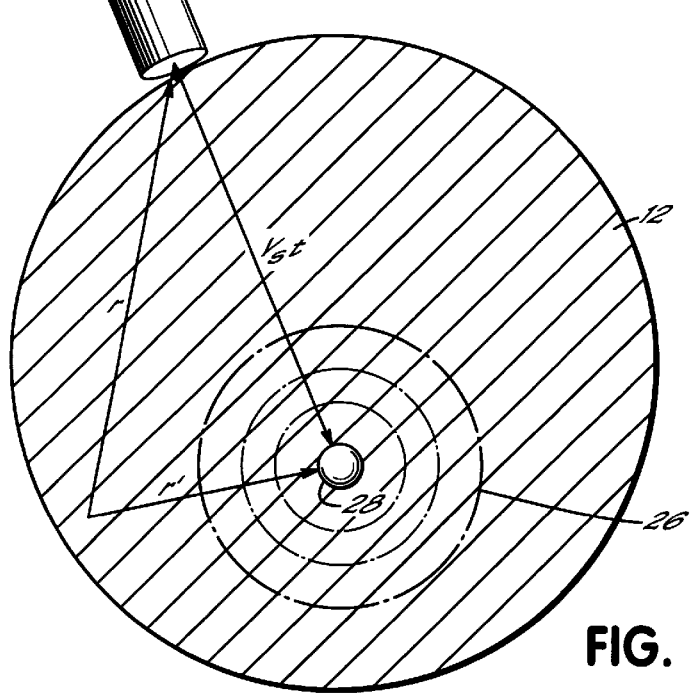
FIG. 10 is an illustration of the coordinate system used in developing a theoretical model for the operation of the scanner of FIG. 1.

The generalized reconstruction geometry is illustrated in FIG. 10. The excess pressure p(r,t) that arrives at position r, where transducer 33 is located, at time t, is the sum of the pressure waves produced at all positions within the tissue. This sum can be expressed as a volume integral:

$$p(r, t) = \frac{\beta\rho}{4\pi} \int\int\int \frac{dr'}{|r-r'|} \frac{\partial^2 T(r', t')}{\partial t^2} \qquad (1)$$

where $\rho$ is the mass density and $\beta$ is the coefficient of thermal expansion of the tissue, the volume integral is carried out over the entire r'-space where the temperature acceleration $\partial^2 T(r',t')/\partial t'^2$ is non-zero, and where $t'=t-|r-r'|/v_s$ ($|r-r'|/v_s$ being the time delay for an acoustic pressure wave to propagate from position r' to position r at the speed of sound in tissue $v_s$).

Under the assumption that the radiation pulse which causes the temperature acceleration is of a duration $\tau$ which is short enough ($\tau<1$ µs) to generate an adiabatic expansion of absorptive tissue, the preceding equation can be rewritten in terms of a regional heat absorption function S(r',t):

$$p(r, t) = \frac{\beta}{4\pi C} \int\int\int \frac{\partial S(r', t')}{\partial t'} \frac{dr'}{|r-r'|} \qquad (2)$$

where C is the specific heat of tissue. We can further write the heating-function as the product of a purely spatial and a purely temporal component, i.e., $$S(r',t')=I_0 A(r')\text{Box}(t',\tau) \qquad (3)$$

where $I_0$ is a scaling factor proportional to the incident radiation intensity, Box(t', $\tau$) represents a pulse of unit height and duration $\tau$, and A(r') represents the fractional energy absorption per unit volume at position r'. Defined in this way $I_0$Box(t',$\tau$) describes the irradiating field and A(r') describes the absorption properties of the medium (breast). The excess pressure can then be written as:

$$p(r, t) = \frac{\beta I_0}{4\pi C} \int\int\int A(r') \frac{d\text{Box}(t')}{dt'} \frac{dr'}{|r-r'|} \qquad (4)$$

Equation 4 expresses how the time-sequential information conveyed by the pressure signal delivers spatial information about the absorption properties of the medium.

Now, note that Box(t') has a value of 1 only from t'=0 to t'=$\tau$. As a result, the integrand on the right side of equation (4) will have a value of zero everywhere except along a thin, spherical "shell" of inner radius $v_s t$ surrounding point r, where 0<t'<$\tau$, i.e., where $|r-r'|/v_s<t<\tau+|r-r'|/v_s$. This thin "shell" has a thickness of $v_s\tau$; accordingly, the volume integral for this thin "shell" can be approximated by $v_s\tau$ multiplied by the surface integral, over the inner surface of the "shell", i.e., where $|r-r'|/v_s=t$, i.e.:

$$p(r, t) \approx v_s\tau \frac{\beta I_0}{4\pi C} \int\int_{t=|r-r'|/v_s} A(r') \frac{dr'}{v_s t} \qquad (5)$$

Equation (5) is valid, provided $\tau$ is short enough. In practice, $\tau<1$ microsecond meets this criterion. Thus, the pressure recorded at position r and time $t=|r-r'|/v_s$ is the sum (integral) of all pressure waves induced over the surface of a sphere of radius $|r-r'|$ due to radiation absorbed at r'.

The objective of the scanner of the present invention is to estimate the fractional absorption distribution A(r') of the tissue being imaged from a set of measured pressure signals p(r,t). To this end, Equation (5) can be recast into a form that resembles a Radon transform:

$$S(r, t) = \frac{4\pi Ct}{\beta I_0 \tau} \int_0^t p(r, t'')dt'' \approx \int\int_{t=|r-r'|/v_s} A(r')dr' \qquad (6)$$

where S(r,t), is the "projection" at the position r, of the absorption which occurs at position r'. Under the condition that $|r-r'|>>d$, where d is the "size" of a typical absorbing object, the spherical surface over which the surface integral of Equation (6) is computed, approximates a plane and Equation (6) approximates a Radon transform. Under this assumption, A(r') can be approximately reconstructed using a three-dimensional inverse Radon transform. The most useful form of the Radon transform is accomplished by:

1. taking the second spatial derivative of each "projection" S(r,t);
2. back-projecting the derivative; and
3. integrating over all projection directions.

Taking the second derivative of S(r,t) with respect to distance x ($x \equiv |r-r'|=v_s t$), yields:

$$\begin{aligned}\frac{\delta^2 S(r, t)}{\delta x^2} &= \frac{1}{v_s^2}\delta^2\frac{S(r, t)}{\delta t^2} \qquad (7)\\ &= \frac{4\pi Ct}{\beta I_0 \tau v_s^2} \frac{\delta^2}{\delta t^2}\left[t\int_{-\infty}^t p(r, t')dt'\right]\\ &= \frac{K}{v_s^2}\left[t\frac{\delta p(r, t)}{\delta t} + 2p(r, t)\right] \equiv S''(r, t)\end{aligned}$$

where K=4 $\pi C/\beta I_0\tau$. So, if we can measure p(r,t) over a sufficient number of positions r, from which we can compute S"(r,t), we can approximately reconstruct the absorption properties A(r') of the object.

Figure 11A:
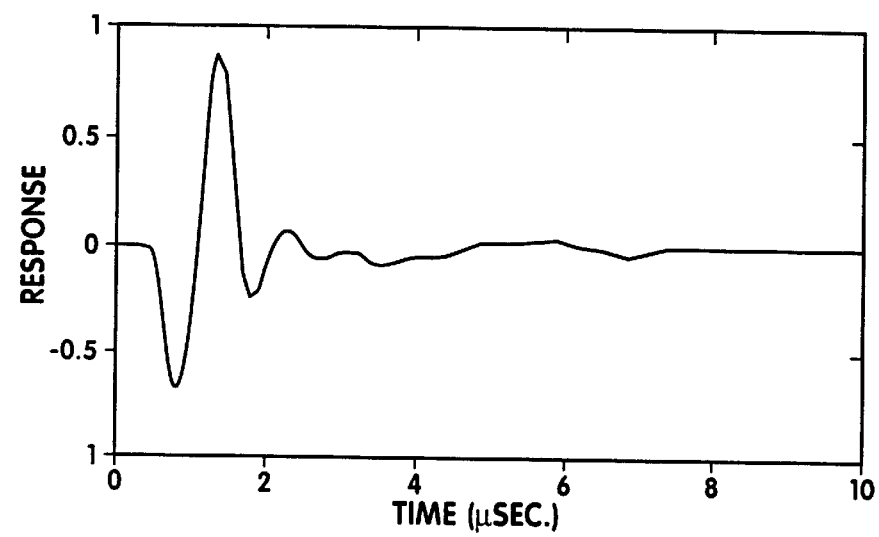
FIG. 11A is a plot of the impulse response of a typical transducer and analog amplification and digital acquisition circuitry.
Figure 11B:
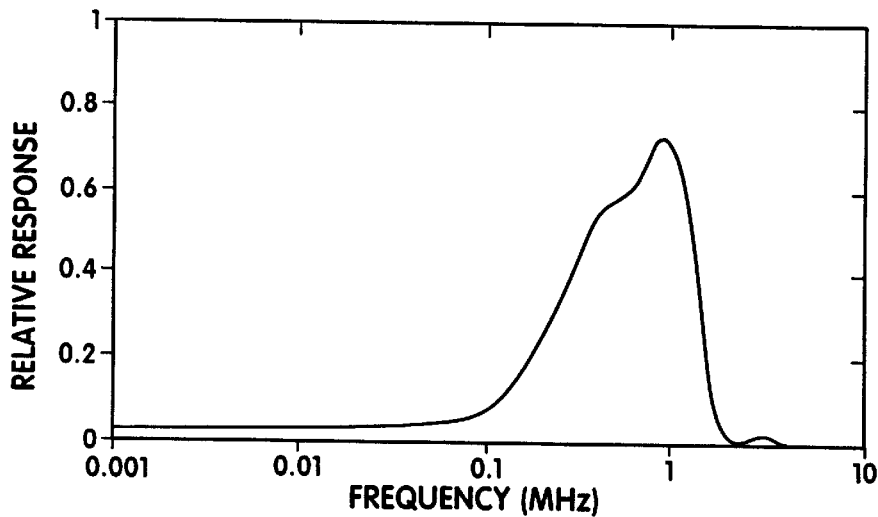
FIG. 11B is a plot of the Fourier transform of the typical transducer response.

In practice, p(r,t) cannot be measured directly because the transducer and associated analog and digital circuitry do not have a flat frequency response. What is actually measured is p'(r,t)=p(r,t)*imp$_r$(t), where imp$_r$(t) is the impulse response of the transducer at position r and * denotes convolution. The impulse response of the transducer can be measured by stimulating the transducer with a narrow 6–10 nanosecond pulse of diffused laser light from an Nd:YAG laser, and collecting the resulting response from the transducer. FIG. 11A illustrates the impulse response of an exemplary transducer and FIG. 11B illustrates the corresponding frequency response obtained by generating the Fourier transformer of the impulse response of FIG. 11A. It can be seen that the frequency response has a substantial relative variation over the passband of the transducer between approximately 100 kHz and 1 MHZ.

Provided the transducers are well-behaved, i.e. have a sufficiently wide bandwidth and no null (or nearly null) frequency response bands, we can compensate for the effect of the response of the transducer. Specifically, prior to computing S''(r,t), we can compute p(r,t) and δp(r,t)/δt from the measured pressure p'(r,t), using the equations:

$$p(r, t) = \mathcal{F}^{-1}\left(\left[\frac{P'(r, \omega)}{I(r, \omega)}\right]\left[\frac{j\omega}{\omega_c}\right]^\alpha \left[1 + \cos\left(\frac{\pi\omega}{\omega_c}\right)\right]^\beta\right) \quad (8)$$

$$\frac{\delta p(r, t)}{\delta t} = \mathcal{F}^{-1}\left(\left[\frac{j\omega P'(r, \omega)}{I(r, \omega)}\right]\left[\frac{j\omega}{\omega_c}\right]^\alpha \left[1 + \cos\left(\frac{\pi\omega}{\omega_c}\right)\right]^\beta\right)$$

where $\mathcal{F}^{-1}$ denotes the inverse Fourier transform, P'(r,ω) is the Fourier transform of measured pressure p'(r,t) and I(r,ω) is the Fourier transform of the transducer/electronics frequency response imp(r,t). The apodizing window function [1+cos(πω/ω$_c$)] is used to taper smoothly high frequency components for noise reduction. For piezo-ceramic transducers we can take $\omega_c = 2\omega_0$, where $\omega_0$ is the "center frequency" of the transducer's response. The exponential factors α and β are used to adjust the relative high frequency and low frequency gain in the images that are produced. α>0 increases the high frequency content and thus enhances edges in the resulting image. β>1 enhances the low frequency content and thus enhances the body of objects that appear in the image. At the present time, factors of α=0 and β=1 have been used in image generation, although other values may be used.

Figure 12A:
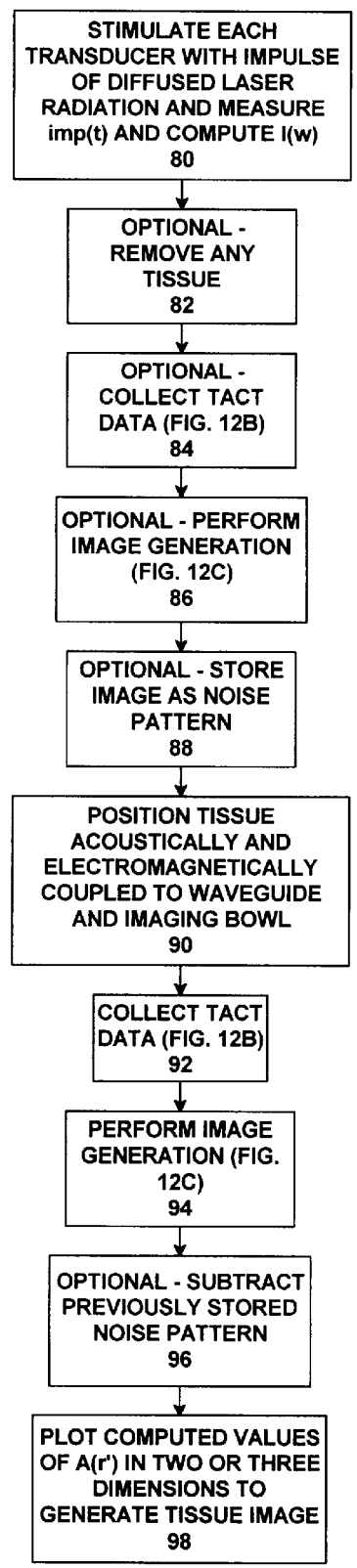
FIG. 12A is a flow chart of the overall operations performed by the scanner of FIG. 1 in producing an image.

Referring now to FIG. 12A, in accordance with the foregoing, image reconstruction is performed. In a first step 80, as noted above, each of the transducers is stimulated with a short pulse of laser light, and the resulting response, which is Imp(t), is collected. This response is then converted via a Fast Fourier Transform (FFT) to the frequency domain function I(ω). This step is performed for each transducer to obtain current frequency response functions I(ω) for each transformer. Step 80 may be performed once and the resulting functions I(ω) used for the lifetime of the scanner, of step 80 may be performed periodically as part of the scanner calibration.

Next, an optional step may be performed to collect an image of any noise pattern in the apparatus. This step may not be necessary if the acoustic behavior of the imaging apparatus substantially reduces noise. To gather an optional noise pattern, in step 82, any tissue is cleared from the scanner. In step 84, the scanner is operated to collect thermoacoustic computed tomography (TACT) data, in the manner described generally above and with more specificity in FIG. 12B, below. Then, the collected TACT data is converted into an image by the backprojecting process described above and in FIG. 12C, below. The resulting image, having been produced without tissue in the scanner, is representative of any noise patterns that are inherent to the scanner. This image is stored in step 88 for subsequent use.

The patterned image stored in step 88, is a consequence of acoustic noise within the scanner that results from electric stimulation of the waveguide 20 and propagation and reflection of the resulting acoustic signals through the imaging bowl 14 and/or through the tank 12. Where there is a significant noise pattern, it has been found to be relatively stable over short periods of time, with variation over longer periods. Accordingly, the noise pattern may be collected, for example, prior to each tissue image, or once per day prior to all tissue imaging that day.

To perform imaging on tissue, in step 90, the tissue sample to be imaged is placed onto the flexible sheet 19 and pressed against the sheet to acoustically and electromagnetically couple the tissue to the waveguide 20 and the transducers 33 in the imaging bowl 14. Then, in step 92, TACT data is again collected, using the procedure described in FIG. 12B. In step 94, the TACT data is converted to an image using the procedure described in FIG. 12C. Then, in an optional step 96, if a noise pattern has previously been generated and stored, the noise pattern is subtracted from the image of the tissue, thus generating an image of the changed acoustic signals resulting from placement of the tissue onto the scanner.

In step 98, the image data is plotted in two or three dimensions so that the tissue may be visualized. As noted below, image data is generated for a cube of 256×256×256 equally spaced in a cube ten centimeters on a side that is centered about the center of curvature of the imaging bowl 14. Regions of other sizes and with other pixel densities can also be computed using the method described herein. In the present example, the computed image data is displayed as a two-dimensional 256×256 pixel image from data points forming a vertical or horizontal "slice" through the tissue.

Figure 12B:
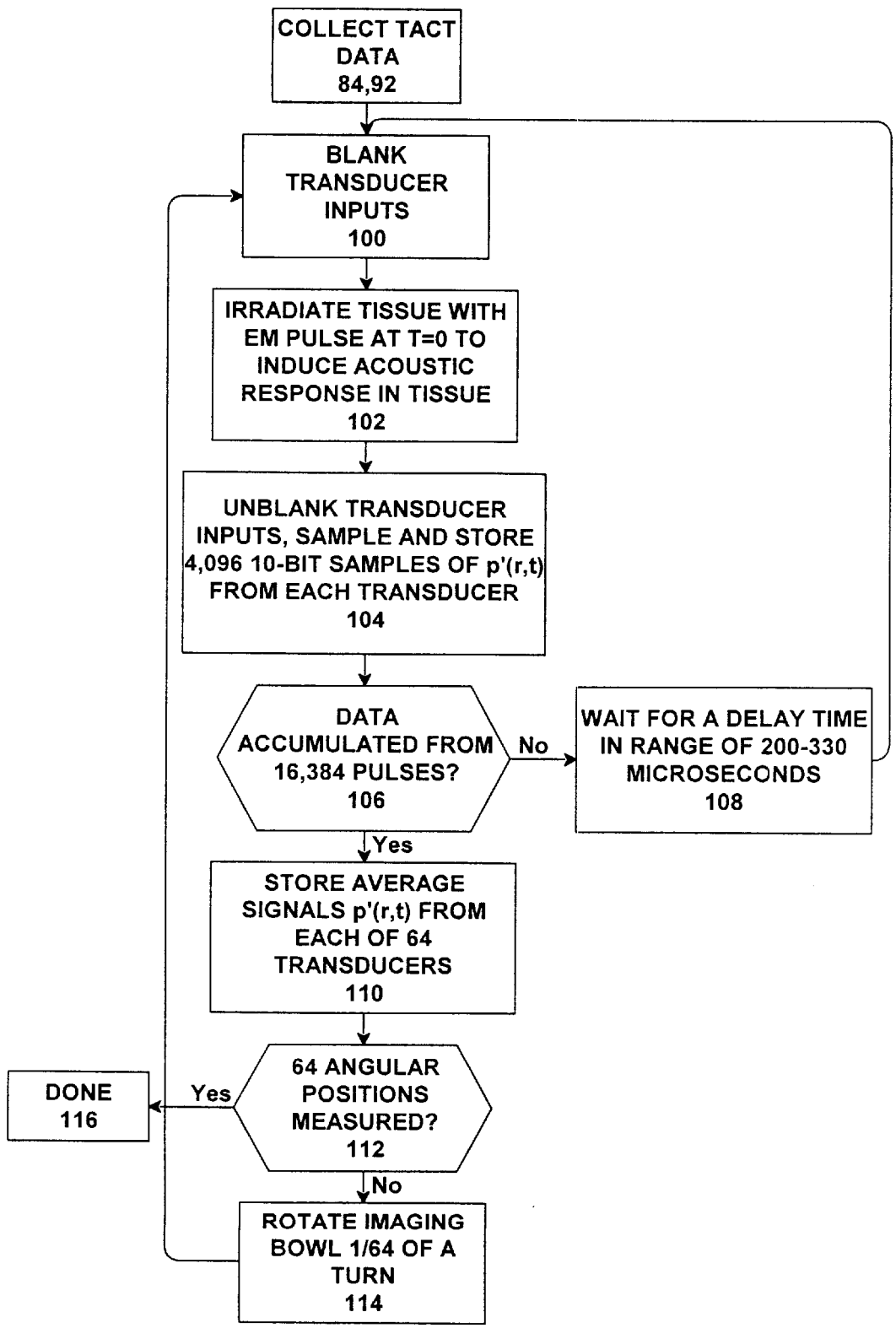
FIGS. 12B and 12C are flow charts of the specific operations involved in collecting TACT data for an image and generating an image from the data, respectively.

Referring now to FIG. 12B, details are provided of the steps 84, 92 in which TACT data is collected. First, in step 100, the transducer inputs are blanked by activating the blanking switches 44 at the input of the transducer amplification circuits. Next in step 102 the microwave generator 22 is energized to produce a short duration pulse, inducing acoustic responses in tissue. Subsequently, before these acoustic signals can propagate to the transducers 33, in step 104 the blanking switches 44 are deactivated so that the transducer signals are delivered to the analog input circuits. The resulting analog signals p'(r,t) are sampled by the 10-bit A/D converter 59 over a period of 409.6 microseconds (4096 samples). These samples are stored into accumulator 61. In step 106 it is determined whether data has been accumulated from 16,384 pulses. If not, in step 108, the scanner waits for a delay time in the range of 200 to 330 microseconds to allow some decrease in the acoustic signals reflecting about the imaging bowl, and then returns to step 100 to generate a new pulse.

The delay time period of step 108, 200 to 330 microseconds, is substantially less than the time period needed for all acoustic echoes within the imaging bowl 14 to dissipate. The acoustic echoes produced after an irradiating pulse is relatively repeatable and can be substantially larger than the thermoacoustic signals that are sought to be captured by the transducers. As a consequence, it has been found that, when the same delay time period were used in each pass through step 108, the noise from preceding pulses completely obliterates the thermoacoustic signals sought to be measured. However, it has been found this difficulty can be avoided by changing the delay time period between pulses, because doing so randomizes the effect of noise from preceding pulses, since the duration between pulses is unique to each measurement, so the echos from preceding pulses occur at different times for each measurement. The result is that the noise from preceding pulses is substantially canceled when the data from 16,384 pulses is averaged together. In one particular embodiment, the length of the delay period is 200 microseconds after the first measurement, and is increased in a linear fashion over the 16,384 measurements so that the delay period is 330 microseconds prior to the last measurement.

After 16,384 measurements have been made and summed by the accumulator 61, processing proceeds from step 106 to step 110, in which the sixty-four accumulated sums from the accumulators 61 in the sixty-four data acquisition channels are stored. These sums represent an average of the 16,384 measured pressure signals received at each of the sixty-four transducers.

After storing the average pressure signals, in step 112 it is determined whether data has been collected for all the sixty-four angular orientations of the imaging bowl. If not, in step 114 the imaging bowl is rotated 1/64 of a complete turn, positioning the transducers for the next set of signal measurements. Processing then returns to step 100 to measure data for another 16,384 pulses. Once data has been collected for all sixty-four angular orientations of the imaging bowl, then the data collection is done (step 116).

Figure 12C:
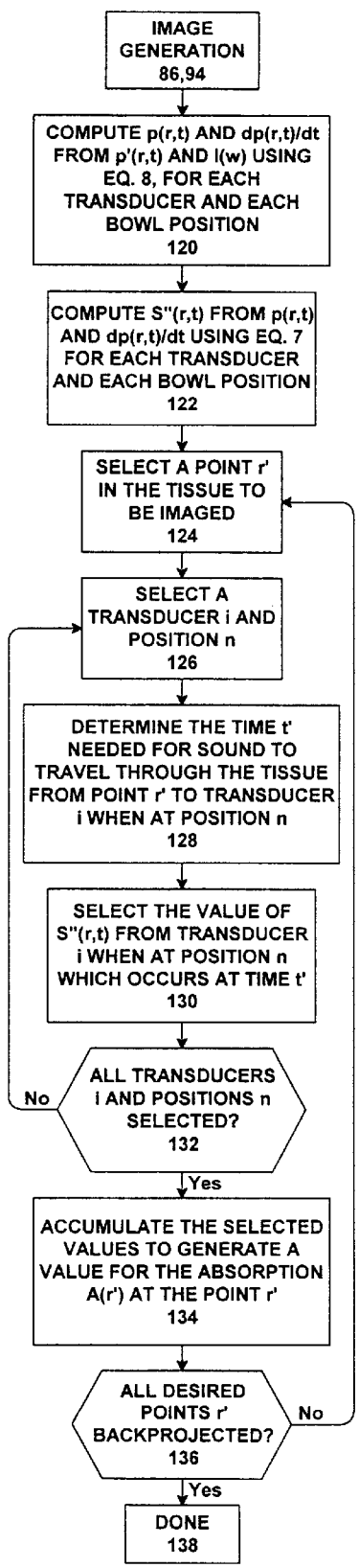

Referring now to FIG. 12C, the process of backprojecting collected TACT data to form images in steps 86 and 94 of FIG. 12A, can be described. In a first step 120, p(r,t) and dp(r,t)/dt are computed from the measured pressures at the transducers p'(r,t), and the frequency transformation of the impulse response I(ω) using Equation 8, recited above. p(r,t) and dp(r,t)/dt are computed from the average waveforms measured for each transducer at each of the sixty-four bowl positions. Next, in step 122, S"(r,t) is computed from p(r,t) and dp(r,t)/dt using Equation 7, recited above. Here again, S"(r,t) is computed for each transformer at each of the sixty-four bowl positions.

After computing values for S"(r,t), these values are back-projected in the loop of steps 124, 126, 128, 130, 132 and 134. In step 124, a point r' to be imaged is selected. This point is, for example, one of the 256×256×256 points in the 10 centimeter square block to be imaged. Next, in step 128, based on the location of this point and the location of a transducer i when in position n, the time t' needed for sound to travel through the tissue and coupling media from the point r' to the transducer is computed, based on the distance traveled and the velocity of sound in tissue/media. Then, in step 130 the value of S"(r,t) for transducer i when in position n, at time t', is selected. Then in step 132 it is determined whether values have been selected from S"(r,t) for all transducers i and all positions n. If not, processing returns to step 126 to select another transducer i and/or position n and identify the appropriate value for t' and appropriate value of S"(r,t).

Once in step 132 values have been selected for all S"(r,t) for all transducers in all positions, then in step 134 the selected values of S"(r,t) are accumulated to generate a value for the absorption A(r') at the point r'. Then in step 136 it is determined whether all of the points r' in the region to be imaged have been backprojected, and if not, processing returns to step 124 to select a new point r' to backproject. Once all points in the region of interest have been backprojected, processing is done (step 138).

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art.

Figure 13:
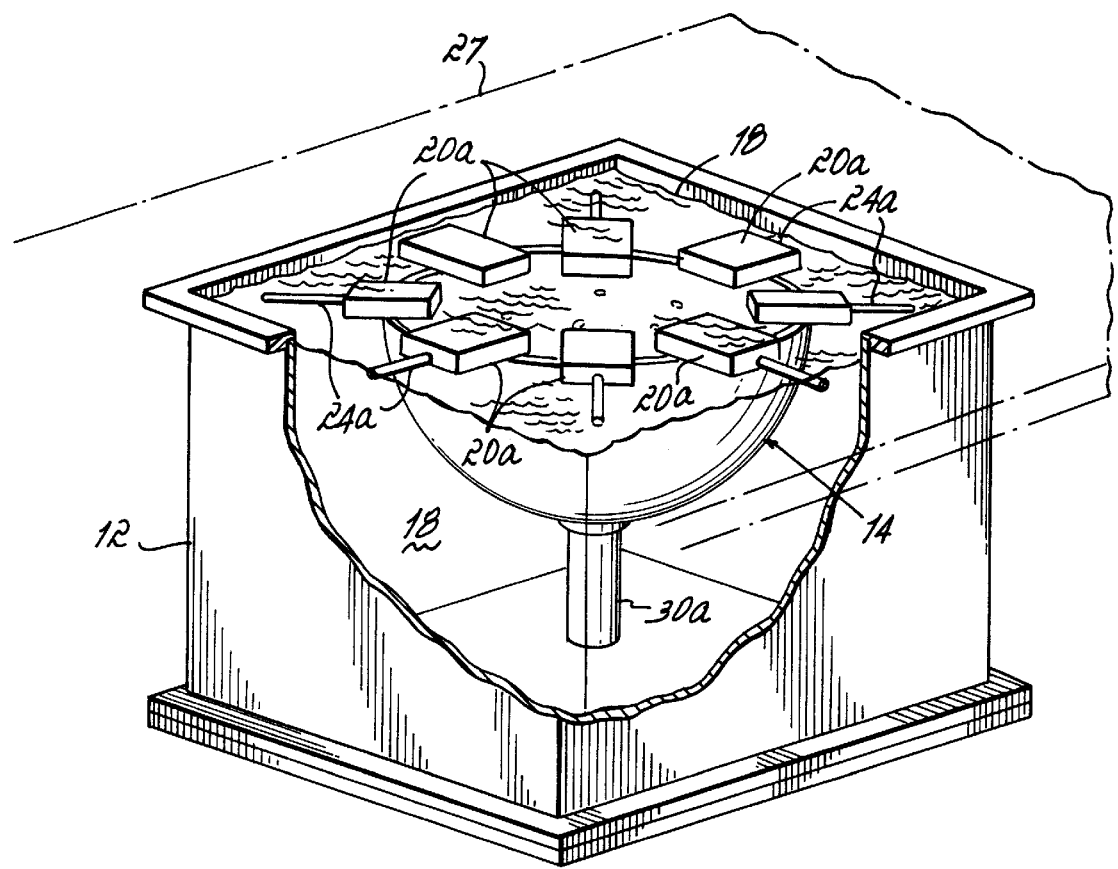
FIG. 13 illustrates a thermoacoustic breast scanner having an alternative microwave waveguide structure in accordance with an alternative embodiment of the invention.

For example, FIG. 13 illustrates an alternative embodiment of the invention, wherein the cylindrical waveguide 20 shown in the previous FIGS. has been replaced with an array of rectangular waveguides 20a immersed in the coupling media around the upper surface of imaging bowl 14, surrounding the opening in table 27 (which has been shown only in phantom). Waveguides 20a are connected via transmission lines 24 to the microwave generator and irradiate the tissue positioned within the imaging bowl 14 with electromagnetic radiation. Although this embodiment does not include a waveguide positioned at the bottom of imaging bowl 14, there remains a cylindrical shell 30a (of reduced diameter) that supports imaging bowl 14 so that bowl 14 can be rotated to appropriately position the transducers.

Further, the array of transducers described herein could be used for ultrasound imaging or combined ultrasound/thermoacoustic imaging. To perform ultrasound imaging, all transducers in the array would be pulsed to produce ultrasound stimulation propagating into the tissue. In a combined ultrasound/thermoacoustic embodiment, the stimulation of the transducers could be provided by the same electromagnetic source as is used to stimulate the tissue. A three dimensional image can then be reconstructed from ultrasound emitted from the transducers and reflected from the tissue.

In this embodiment, all transducers are pulsed simultaneously, and following this pulse, acoustic signals received at the transducers are converted to digital values. The acoustic signals are collected for a period of time a little longer than the time a reflected echo would take to travel round-trip between any transducer and the farthest section of the imaging volume. This period of time might be on the order of 200 microseconds.

Denote the digitized set of signals received by the transducers as $S_j(t_k)$, where j denotes the transformer number and $t_k$ denotes the duration of time after the excitation pulse (i.e., the excitation pulse occurs at $t_k=0$). A three dimensional image can be formed by summing the reflected echo signals from all N transducers that reflect at each position within the imaging volume. For an arbitrary position l within the imaging volume, the round-trip distance $D_{jl}$ between position l and transducer j is known (note that this distance is twice the distance utilized in backprojection of thermoacoustic responses of tissue, as discussed above). The total reflected energy received by the transducer array from reflections of acoustic energy produced by each transducer, reflected at position l, and received by the same transducer, can be estimated as $$I_l = \sum_{j=1}^{N} S_j\left(\frac{D_{jl}}{v_s}\right),$$

where $v_s$ is the velocity of sound, and $I_l$ is a backprojected estimate of the sum, for all N transducers, of energy reflected at the point l. Pre-processing can be performed on the $S_j(t_k)$ before imaging, as discussed above; for example, impulse response filtering, or envelope detection can be performed on the $S_j(t_k)$, and/or the first or second temporal derivative of $S_j(t_k)$ can be computed prior to back-projection. The transducer array can be rotated as described above during data acquisition in order to collect data from additional locations and effectively increase the number of transducers.

The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. Apparatus for imaging tissue structures by detecting acoustic waves in the tissue, comprising
   a tank containing a coupling media having an acoustic characteristic impedance which is substantially similar to that of the tissue to reduce reflections of acoustic waves impinging into the coupling media from the tissue;

a plastic, three-dimensional curved surface immersed in the tank and positioned opposite to the tissue; and a plurality of acoustic sensors positioned upon the three dimensional curved surface and directed toward the tissue to detect acoustic waves in the tissue.

2. The apparatus of claim 1 further comprising mountings of acoustically absorbent material, wherein said acoustic sensors are attached to said mountings and said mountings are attached to said curved surface.

3. The apparatus of claim 2 wherein said acoustic sensors are cylindrical in shape and said mountings are collars surrounding said acoustic sensors.

4. The apparatus of claim 1 further comprising baffling surrounding an interior surface of said tank.

5. The apparatus of claim 1 further comprising a waveguide for waveguide positioned inside of said tank, and baffling surrounding said waveguide.

6. The apparatus of claim 1 further comprising a motor connected to the curved surface and moving the surface to collect acoustic waves from the sensors in a plurality of locations.

7. The apparatus of claim 6 wherein the motor is a rotating motor and rotates the curved surface and sensor to a plurality of rotational positions.

8. The apparatus of claim 1 wherein the curved surface is spherically curved.

9. The apparatus of claim 1 wherein the sensors are positioned on the curved surface along a spiral path.

10. The apparatus of claim 1 further comprising an electromagnetic radiation source positioned inside of the tank and immersed in the coupling media, and wherein the plastic curved surface is coated with a conductive material and forms a ground plane for the electromagnetic radiation source.

11. A method for imaging tissue structures by detecting acoustic waves in the tissue, comprising immersing the tissue in a coupling media having an acoustic characteristic impedance which is substantially similar to that of the tissue to reduce reflections of acoustic waves impinging into the coupling media from the tissue;

immersing a three-dimensional plastic curved surface immersed in the coupling media positioned opposite to the tissue; and detecting acoustic waves in the tissue with a plurality of acoustic sensors positioned upon the three dimensional curved surface.

12. The method of claim 11 further comprising attaching said acoustic sensors to mountings of acoustically absorbent material, and attaching said mountings to said curved surface.

13. The method of claim 12 wherein said acoustic sensors are cylindrical in shape and said mountings are collars surrounding said acoustic sensors.

14. The method of claim 11 further comprising baffling an interior surface of said tank.

15. The method of claim 11 further comprising positioning a waveguide inside of said tank, and surrounding said waveguide with baffling.

16. The method of claim 11 further comprising moving the curved surface to a plurality of locations and collecting acoustic waves with the sensors in each of the plurality of locations.

17. The method of claim 16 wherein moving the curved surface to a plurality of locations comprises rotating the curved surface to a plurality of rotary positions.

18. The method of one of claims 11 wherein the curved surface is spherically curved.

19. The method of one of claims 11 wherein the sensors are positioned on the curved surface along a spiral path.

20. The method of one of claims 11 further comprising irradiating the tissue with an electromagnetic radiation source positioned inside of the tank and immersed in the coupling media, wherein the curved surface is conductive and forms a ground plane for the electromagnetic radiation source.

21. Apparatus for imaging tissue structures by detecting acoustic waves in the tissue, comprising a tank containing a coupling media having an acoustic characteristic impedance which is substantially similar to that of the tissue to reduce reflections of acoustic waves impinging into the coupling media from the tissue;

a spherically curved surface immersed in the tank and positioned opposite to the tissue, the surface having a center of curvature and axis of symmetry, and a plurality of acoustic sensors positioned upon the three dimensional curved surface directed toward the tissue to detect acoustic waves in the tissue, each sensor positioned at an angle $\phi$ relative to said axis of symmetry measured from said center of curvature, and at an angle $\theta$ relative to a reference plane including said axis of symmetry, said sensors positioned along a spiral path and substantially equally spaced in $\phi$ and $\cos \theta$.

22. The apparatus of claim 21 further comprising a motor connected to the curved surface and moving the surface to collect acoustic waves from the sensors in a plurality of locations.

23. The apparatus of claim 22 wherein the motor is a rotating motor and rotates the curved surface and sensor to a plurality of rotational positions.

24. The apparatus of claim 21 further comprising an electromagnetic radiation source positioned inside of the tank and immersed in the coupling media, and wherein the plastic curved surface is coated with a conductive material and forms a ground plane for the electromagnetic radiation source.

25. A method for imaging tissue structures by detecting acoustic waves in the tissue, comprising immersing the tissue in a coupling media having an acoustic characteristic impedance which is substantially similar to that of the tissue to reduce reflections of acoustic waves impinging into the coupling media from the tissue;

immersing a spherically curved surface in the coupling media positioned opposite to the tissue, the surface having a center of curvature and axis of symmetry, and detecting acoustic waves in the tissue with a plurality of acoustic sensors positioned upon the three dimensional curved surface directed toward the tissue, each sensor positioned at an angle $\phi$ relative to said axis of symmetry measured from said center of curvature, and at an angle $\theta$ relative to a reference plane including said axis of symmetry, said sensors positioned along a spiral path and substantially equally spaced in $\phi$ and $\cos \theta$.

26. The method of claim 25 further comprising moving the curved surface to a plurality of locations and collecting acoustic waves with the sensors in each of the plurality of locations.

27. The method of claim 26 wherein moving the curved surface to a plurality of locations comprises rotating the curved surface to a plurality of rotary positions.

28. The method of one of claims 25 further comprising irradiating the tissue with an electromagnetic radiation source positioned inside of the tank and immersed in the coupling media, wherein the curved surface is conductive and forms a ground plane for the electromagnetic radiation source.

29. Apparatus for imaging tissue structures by detecting localized absorption of electromagnetic waves in said tissue, comprising
- a tank containing a coupling media having an acoustic characteristic impedance which is substantially similar to that of said tissue to reduce reflections of acoustic waves impinging into said media from said tissue, and having an electromagnetic characteristic impedance which is substantially similar to that of said tissue to reduce reflections of electromagnetic waves impinging into said tissue from said coupling media;
- a waveguide positioned inside of said tank and immersed in said coupling media;
- a plurality of acoustic sensors positioned on a surface within said tank and immersed in said coupling media;
- RF power circuitry supplying electromagnetic radiation to said waveguide to produce a pulse of electromagnetic radiation within said tissue; and
- computing circuitry detecting resultant pressure waveforms arriving at said acoustic sensors, storing data representative of said waveforms, and combining a plurality of said detected pressure waveforms to derive an image, points in said image being derived by combining measures of pressure waveforms originating at points within said tissue.

30. The apparatus of claim 29 wherein said waveguide is a cylindrical waveguide extending from said surface.

31. The apparatus of claim 29 wherein said waveguide is a rectangular waveguide extending from said surface.

32. The apparatus of claim 29 wherein said sensors are piezoelectric transducers.

33. The apparatus of claim 29 wherein said sensors are evenly spaced across said surface.

34. The apparatus of claim 29 further comprising a motor coupled to said surface for moving said surface and said sensors to generate said image of said tissue.

35. The apparatus of claim 34 wherein said motor moves said surface in a rectilinear fashion.

36. The apparatus of claim 34 wherein said motor rotates said surface.

37. The apparatus of claim 36 wherein said sensors are positioned on said surface along a spiral path.

38. The apparatus of claim 29 wherein said tank includes an open top surface whereby said tissue may be received into said acoustic coupling media.

39. The apparatus of claim 38 wherein said tank further comprises a flexible film cover enclosing said tank to contain said acoustic coupling media, whereby said tissue may be pressed upon said flexible film to couple acoustic waves into said acoustic coupling media.

40. A method for imaging tissue structures by detecting localized absorption of electromagnetic waves in said tissue, comprising
- filling a tank with a coupling media having an acoustic characteristic impedance which is substantially similar to that of said tissue to reduce reflections of acoustic waves impinging into said media from said tissue, and having an electromagnetic characteristic impedance which is substantially similar to that of said tissue to reduce reflections of electromagnetic waves impinging into said tissue from said coupling media;
- immersing a waveguide in said coupling media positioned inside of said tank;
- positioning a plurality of acoustic sensors on a surface within said tank and immersed in said coupling media;
- immersing said tissue in said coupling media and supplying electromagnetic radiation to said waveguide to produce a pulse of electromagnetic radiation within said tissue; and
- detecting resultant pressure waveforms arriving at said acoustic sensors, storing data representative of said waveforms, and combining a plurality of said detected pressure waveforms to derive an image, points in said image being derived by combining measures of pressure waveforms originating at points within said tissue.

41. The method of claim 40 wherein said waveguide is a cylindrical waveguide extending from said surface.

42. The method of claim 40 wherein said waveguide is a rectangular waveguide extending from said surface.

43. The method of claim 40 wherein said sensors are piezoelectric transducers.

44. The method of claim 40 wherein said sensors are positioned evenly spaced across said surface.

45. The method of claim 40 further comprising moving said surface and said sensors to generate said image of said tissue.

46. The method of claim 45 wherein said surface is moved in a rectilinear fashion.

47. The method of claim 45 wherein said surface is rotated.

48. The method of claim 47 wherein said sensors are positioned on said surface along a spiral path.

49. The method of claim 40 wherein said tank includes an open top surface and further comprising positioning said tissue into said acoustic coupling media via said open top surface.

50. The method of claim 49 wherein said tank further comprises a flexible film cover enclosing said tank to contain said acoustic coupling media, and further comprising pressing said tissue upon said flexible film to couple acoustic waves into said acoustic coupling media.

51. Apparatus for imaging tissue structures by detecting localized absorption of electromagnetic waves in said tissue, comprising
- a tank containing a coupling media;
- an electromagnetic source;
- a plurality of acoustic sensors positioned within said tank and immersed in said coupling media;
- RF power circuitry supplying electromagnetic radiation to said electromagnetic source to produce a pulse of electromagnetic radiation within said tissue; and
- computing circuitry detecting resultant pressure waveforms arriving at said acoustic sensors, storing data representative of said waveforms, and combining a plurality of said detected pressure waveforms to derive an image, points in said image being derived by combining measures of pressure waveforms originating at points within said tissue,
- wherein said computing circuitry collects pressure waveforms arriving at said acoustic sensors in the absence of tissue, and collects pressure waveforms arriving at said acoustic sensors with tissue present, and derives an image of tissue based on a comparison of responses achieved with tissue present and in the absence of tissue.

52. The apparatus of claim 51 wherein said sensors are piezoelectric transducers.

53. The apparatus of claim 51 wherein said sensors are positioned on a surface.

54. The apparatus of claim 53 further comprising a motor coupled to said surface for moving said surface and said sensors to collect pressure waveforms.

55. The apparatus of claim 54 wherein said motor moves said surface in a rectilinear fashion.

56. The apparatus of claim 54 wherein said motor rotates said surface.

57. The apparatus of claim 56 wherein said sensors are positioned on said surface along a spiral path.

58. The apparatus of claim 51 wherein said tank includes an open top surface whereby said tissue may be received into said coupling media.

59. The apparatus of claim 58 wherein said tank further comprises a flexible film cover enclosing said tank to contain said coupling media, whereby said tissue may be pressed upon said flexible film to couple acoustic waves into said coupling media.

60. A method for imaging tissue structures by detecting localized absorption of electromagnetic waves in said tissue, comprising providing an electromagnetic source;

immersing a plurality of acoustic sensors in a coupling media;

immersing said tissue in said coupling media and supplying electromagnetic radiation to said electromagnetic source to produce a pulse of electromagnetic radiation within said tissue; and detecting resultant pressure waveforms arriving at said acoustic sensors, storing data representative of said waveforms, and removing said tissue from said coupling media and detecting resultant pressure waveforns, combining a plurality of said detected pressure waveforms to derive an image, points in said image being derived by combining measures of pressure waveforms originating at points within said tissue, said image being derived based on a comparison of responses achieved with tissue present and in the absence of tissue.

61. The method of claim 60 wherein said sensors are piezoelectric transducers.

62. The method of claim 60 wherein said sensors are positioned on a surface.

63. The method of claim 62 further comprising moving said surface and said sensors to collect pressure waveforms.

64. The method of claim 63 wherein said surface is moved in a rectilinear fashion.

65. The method of claim 63 wherein said surface is rotated.

66. The method of claim 65 wherein said sensors are positioned on said surface along a spiral path.

67. The method of claim 60 further comprising providing a flexible film cover enclosing said coupling media, and pressing said tissue upon said flexible film to couple acoustic waves into said coupling media.

68. Apparatus for imaging tissue structures by detecting localized absorption of electromagnetic waves in said tissue, comprising a tank containing a coupling media;

an electromagnetic source;

a plurality of acoustic sensors positioned within said tank and immersed in said coupling media;

RF power circuitry supplying electromagnetic radiation to said electromagnetic source at irregular intervals, to produce a series of pulses of electromagnetic radiation within said tissue; and computing circuitry detecting resultant pressure waveforms arriving at said acoustic sensors for each of said series of pulses, storing data representative of said waveforms, and combining a plurality of said detected pressure waveforms to derive an image, points in said image being derived by combining measures of pressure waveforms originating at points within said tissue.

69. The apparatus of claim 68 wherein said sensors are piezoelectric transducers.

70. The apparatus of claim 68 wherein said sensors are positioned on a surface.

71. The apparatus of claim 70 further comprising a motor coupled to said surface for moving said surface and said sensors to collect pressure waveforms.

72. The apparatus of claim 71 wherein said motor moves said surface in a rectilinear fashion.

73. The apparatus of claim 71 wherein said motor rotates said surface.

74. The apparatus of claim 73 wherein said sensors are positioned on said surface along a spiral path.

75. The apparatus of claim 68 wherein said tank includes an open top surface whereby said tissue may be received into said coupling media.

76. The apparatus of claim 75 wherein said tank further comprises a flexible film cover enclosing said tank to contain said coupling media, whereby said tissue may be pressed upon said flexible film to couple acoustic waves into said coupling media.

77. A method for imaging tissue structures by detecting localized absorption of electromagnetic waves in said tissue, comprising providing an electromagnetic source;

immersing a plurality of acoustic sensors in a coupling media;

immersing said tissue in said coupling media and supplying electromagnetic radiation to said electromagnetic source at irregular intervals, to produce a series of pulses of electromagnetic radiation within said tissue; and detecting resultant pressure waveforms arriving at said acoustic sensors for each of said series of pulses, storing data representative of said waveforms, and combining a plurality of said detected pressure waveforms to derive an image, points in said image being derived by combining measures of pressure waveforms originating at points within said tissue.

78. The method of claim 77 wherein said sensors are piezoelectric transducers.

79. The method of claim 77 wherein said sensors are positioned on a surface.

80. The method of claim 79 further comprising moving said surface and said sensors to collect pressure waveforms.

81. The method of claim 80 wherein said surface is moved in a rectilinear fashion.

82. The method of claim 80 wherein said surface is rotated.

83. The method of claim 82 wherein said sensors are positioned on said surface along a spiral path.

84. The method of claim 77 further comprising providing a flexible film cover enclosing said coupling media, and pressing said tissue upon said flexible film to couple acoustic waves into said coupling media.

85. Apparatus for imaging tissue structures by detecting localized absorption of electromagnetic waves in said tissue, comprising a tank containing a coupling media;

an electromagnetic source;

a plurality of acoustic sensors positioned within said tank and immersed in said coupling media;

RF power circuitry supplying electromagnetic radiation to said electromagnetic source, to produce a pulse of electromagnetic radiation within said tissue; and computing circuitry detecting resultant pressure waveforms arriving at said acoustic sensors, storing data representative of said waveforms, filtering said waveforms using a filter derived from a measured impulse response of an acoustic sensor, and combining a plurality of said filtered detected pressure waveforms to derive an image, points in said image being derived by combining measures of pressure waveforms originating at points within said tissue.

86. The apparatus of claim 85 wherein said sensors are piezoelectric transducers.

87. The apparatus of claim 85 wherein said sensors are positioned on a surface.

88. The apparatus of claim 87 further comprising a motor coupled to said surface for moving said surface and said sensors to collect pressure waveforms.

89. The apparatus of claim 88 wherein said motor moves said surface in a rectilinear fashion.

90. The apparatus of claim 88 wherein said motor rotates said surface.

91. The apparatus of claim 90 wherein said sensors are positioned on said surface along a spiral path.

92. The apparatus of claim 85 wherein said tank includes an open top surface whereby said tissue may be received into said coupling media.

93. The apparatus of claim 92 wherein said tank further comprises a flexible film cover enclosing said tank to contain said coupling media, whereby said tissue may be pressed upon said flexible film to couple acoustic waves into said coupling media.

94. A method for imaging tissue structures by detecting localized absorption of electromagnetic waves in said tissue, comprising providing an electromagnetic source;

immersing a plurality of acoustic sensors in a coupling media;

measuring an impulse response of an acoustic sensor;

immersing said tissue in said coupling media and supplying electromagnetic radiation to said electromagnetic source, to produce a pulse of electromagnetic radiation within said tissue; and detecting resultant pressure waveforms arriving at said acoustic sensors, storing data representative of said waveforms, filtering said waveforms using a filter derived from a measured impulse response of an acoustic sensor, and combining a plurality of said filtered detected pressure waveforms to derive an image, points in said image being derived by combining measures of pressure waveforms originating at points within said tissue.

95. The method of claim 94 wherein said sensors are piezoelectric transducers.

96. The method of claim 94 wherein said sensors are positioned on a surface.

97. The method of claim 96 further comprising moving said surface and said sensors to collect pressure waveforms.

98. The method of claim 97 wherein said surface is moved in a rectilinear fashion.

99. The method of claim 97 wherein said surface is rotated.

100. The method of claim 99 wherein said sensors are positioned on said surface along a spiral path.

101. The method of claim 94 further comprising providing a flexible film cover enclosing said coupling media, and pressing said tissue upon said flexible film to couple acoustic waves into said coupling media.

* * * * *